(12) United States Patent
Gu et al.

(10) Patent No.: US 7,691,263 B1
(45) Date of Patent: Apr. 6, 2010

(54) MONOLITHIC COLUMN TECHNOLOGY FOR LIQUID CHROMATOGRAPHY

(75) Inventors: Binghe Gu, Provo, UT (US); Milton L. Lee, Pleasant Grove, UT (US)

(73) Assignee: Brigham Young University, Provo, UT (US)

( * ) Notice: Subject to any disclaimer, the term of this patent is extended or adjusted under 35 U.S.C. 154(b) by 245 days.

(21) Appl. No.: 11/437,841

(22) Filed: May 19, 2006

Related U.S. Application Data

(60) Provisional application No. 60/683,063, filed on May 20, 2005.

(51) Int. Cl.
B01D 15/08 (2006.01)

(52) U.S. Cl. .................. 210/198.2; 210/502.1; 210/635; 210/656

(58) Field of Classification Search ............. 210/198.2, 210/635, 656, 659, 502.1; 502/402
See application file for complete search history.

(56) References Cited

U.S. PATENT DOCUMENTS

| | | | | |
|---|---|---|---|---|
| 4,468,330 | A * | 8/1984 | Kamiyama et al. | 210/656 |
| 5,053,135 | A * | 10/1991 | Boschetti et al. | 210/635 |
| 5,647,979 | A * | 7/1997 | Liao et al. | 210/198.2 |
| 5,935,429 | A * | 8/1999 | Liao et al. | 210/198.2 |
| 6,440,284 | B1 * | 8/2002 | Dubrow | 204/455 |
| 6,887,384 | B1 * | 5/2005 | Frechet et al. | 210/634 |
| 2004/0000522 | A1 * | 1/2004 | Xie et al. | 210/656 |

OTHER PUBLICATIONS

C. J.R. Morris, P. Morris, Separation Methods in Biochemistry. Wiley, New York, 1976, p. 413-470.
S. Hjerten, M.J. Zhu, J. Chromatogr. 346 (1985) 265.
S. Hjerten, J. Chromatogr. 347 (1985) 191.
N.J. Clarke, A.J. Tomlinson, G. Schomburg, S. Naylor, Anal. Chem. 69 (1997) 2786.
N. Iki, E.S. Yeung, J. Chromatogr A 731 (1996) 273.
J. Preisler, E.S. Yeung, Anal. Chem. 68 (1996) 2885.
R. McCormick, Anal. Chem. 60 (1988) 2322.
Z. Zhao, A. Malik, M.L. Lee, Anal. Chem. 65 (1993) 2747.
R.G. Chapman, E. Ostuni, M.N. Liang, G. Meluleni, E. Kim, L. Yan, G. Pier, H.S. Warren, G.M. Whitesides, Langmuir 17 (2001) 1225.
E. Ostuni, R.G. Chapman, R.E., Holmlin, S. Takayama, G.M. Whitesides, Langmuir 17 (2001) 5605.
E. Ostuni, R.G. Chapman, M.N. Liang, G. Meluleni, G. Pier, D.E. Ingber, G.M. Whitesides, Langmuir 17 (2001) 6336.
T. Zewert, M. Harrington, Electrophoresis 13 (1992) 817.
T. Zewert, M. Harrington, Electrophoresis 13 (1992) 824.
J.V. Darkins, N. P. Gabbott, Polymer 22 (1981) 291.

(Continued)

*Primary Examiner*—Ernest G Therkorn
(74) *Attorney, Agent, or Firm*—James Sonntag

(57) ABSTRACT

A monolith for liquid chromatography is disclosed that involves a reaction product of; a (1) crosslinker having at least three adjacent groups, selected from ethylene oxide, polyethylene oxide, and mixtures thereof, and two or more pendent vinyl groups, and (2) monomer having the formula, $CH_2=CR-Y-Z$, where R is H or $CH_3$, where Z is a functional group selected to impart a desired interaction property to the monolith, and where Y is nothing, or any group that will not materially affect or compete with the function of the functional group (Z) in the monolith, or the reactivity of vinyl groups in the crosslinker or monomer.

16 Claims, 12 Drawing Sheets

OTHER PUBLICATIONS

S. Hjertén, J.L. Liao, R. Zhang, J. Chromatogr. 473 (1989) 273.
S.M. Fields, Anal. Chem. 68 (1996) 2709.
H. Minakuchi, K. Nakanishi, N. Soga, N. Ishizuka, N. Tanaka, Anal. Chem. 68 (1996) 3498.
F. Svec, J.M.J. Fréchet, Anal. Chem. 54 (1992) 820.
S, Xie, F. Svec, J.M.J, Fréchet, J. Polym. Sci. A: Polym. Chem. 35 (1997) 1013.
C. Yu, M.H. Davey, F. Svec, J.M.J. Fréchet, Anal. Chem. 73 (2001) 5088.
P.H. Humble, R.T. Kelly, A.T. Woolley, H.D. Tolley, M.L. Lee, Anal. Chem. 76 (2004) 5641.
C. Yu, M. Xu, F. Svec, J.M.J. Fréchet, J. Polym. Sci. A: Polym. Chem. 40 (2002) 755.
D.S. Peterson, T. Rohr, F. Svec, J.M.J. Fréchet, Anal. Chem. 74 (2002) 4081.
J.J. Meyers, Al Liapis, J. Chromatogr. A 852 (1999) 3.
A.I. Liapis, J.J. Meyers, O.K. Crosser, J. Chromatogr. A 865 (1999) 13.
F. Nevejans, M. Verzele, J. Chromatogr. 350 (1985) 145.
C.T. Mant, R.S. Hodges (Editors), High-Performance Liquid Chromatography of Peptides and Proteins: Separation, Analysis, and Conformation. CRC Press, Boca Raton, FL, 1991, p. 139-142.
G. Szabo, K. Offenmuller, E. Csato, Anal. Chem. 60 (1988) 213.
S. Lubbad, M.R. Buchmeiser, Macromol. Rapid Commun. 23 (2002) 617.
I. Halasz, K. Martin, Angwew. Chem. (Int. Ed. Engl.) 17 (1978) 901.
I. Halasz, K. Martin, Angwew. Chem. (Int. Ed. Engl.) 17 (1978) 901.
D.E. Schmidt, R. Glese, D. Conron, B. Karger, Anal. Chem. 52 (1980) 177.
J.K. Towns, F.E. Regnier, Anal. Chem. 63 (1991) 1126.
K.K.C. Yeung, C.A. Lucy, Anal. Chem. 69 (1997) 3435.
J. Cunliffe, N.E. Baryla, C.A. Lucy, Anal. Chem. 74 (2002) 776.
C.T. Culbertson, J.W. Jorgensen, Anal. Chem. 66 (1994) 955.
D.G. McLaren, D.D. Chen, Electrophoresis, 24 (2003) 2887.
Kimura, H.; Tanigawi, T.; Morisaka, H.; Ikegami, T.; Hosoya, K.; Ishizuka, N.; Minakuchi, H.; Nakanishi, K.; Ueda, M.; Cabrera, K.; Tanaka, N. J. Sep. Sci. 2004, 27, 897-904.
Gu, B; Armenta, J. M.; Lee, M. L. J. Chromatogr. A 2005, 1079, 382-391.
Guyot, A.; Bartholin, M. Prog. Polym. Sci. 1982, 8, 277-332.
Sederel, W. L.; Jong, G. J. J. Appl. Polym. Sci. 1973, 17, 2835-2846.
Kun, K. A.; Kunin, R. J. Polym. Sci.: Part A1 1968, 6, 2689-2701.
Svec, F. LC-GC, Europe 2003, 16(6a), 24-28.
Svec, F. J. Sep. Sci. 2004, 27, 747-766.
Svec, F. J. Sep. Sci. 2004, 27, 1419-1430.
Burke, T. W. L.; Mant, C. T.; Black, J. A.; Hodges, R. S. J. Chromatogr. 1989, 476, 377-389.
Mant, C. T.; Hodges, R. S. In High-Performance Liquid Chromatography of Peptides and Proteins: Separation, Analysis, and Conformation; Mant, C. T.; Hodges, R. S., Ed.; CRC Press: Boca Raton, 1991; pp. 171-185.
Alpert, A. J.; Andrews, P. C. J. Chromatogr. 1988, 443, 85-96.
Imamura, T.; Sugihara, J.; Yokata, E.; Kagimoto, M.; Naito, Y.; Yanase, T. J. Chromatogr. 1984, 305, 456-460.
Kawasaki, H.; Imajoh, S.; Suzuki, K. J. Biochem. 1987, 102, 393-400.
Binghe Gu, et al., "Preparation and evaluation of poly(polyethylene glycol methyl ether acrylate-co-polyethylene glycol diacrylate) monolith for protein analysis" Journal of Chromatography A., Mar. 29, 2005, 1079 (2005) 382-391, Elsevier B.V.
Binghe Gu, et al., "Efficient polymer monolith for strong cation-exchnage capillary liquid chromatography of peptides" Apr. 27, 2006, 2006, Anal. Chem. 78, 3509-3518, American Chemical Society.
Stadalius, A. A.; Quarry, M. A.; Snyder, L. R. J. Chromatogr. 1985, 327, 93-113.
Mant, C. T.; Hodges, R. S. In High-Performance Liquid Chromatography of Biological Macromolecules: Methods and Applications; Gooding, K.; Regnier, F., Eds.; Marcel Dekker: New York, 1990; pp. 301-332.
Mant, C. T.; Hodges, R. S. J. Chromatogr. 1985, 326, 349-356.
Mant, C. T.; Hodges, R. S. J. Chromatogr. 1985, 327, 147-155.
Crimmins, D. L.; Thoma, R. S.; McCourt, D. W.; Schwartz, B. D. Anal. Biochem. 1989, 176, 255-260.
Crimmins, D. L.; Gorka, J.; Thoma, R. S.; Schwartz, B. D. J. Chromatogr. 1988, 443, 63-71.
Viklund, C.; Svec, F.; Fréchet, J. M. J. Biotechnol. Prog. 1997, 13, 597-600.
Ueki, Y.; Umemura, T.; Li, J.; Odake, T.; Tsunoda, K. Anal. Chem. 2004, 76, 7007-7012.
Zakaria, P.; Hutchinson, J. P.; Avdalovic, N.; Liu, Y.; Haddad, P. R. Anal. Chem. 2005, 77, 417-423.
Hilder, E. F.; Svec, F.; Fréchet, J. M. J. J. Chromatogr. A 2004, 1053, 101-106.
Righetti, P. G. in Immobilized pH Gradients. Theory and Methodology; Burdon, R. H.; van Knippenberg, P. H., Eds.; Elsevier: New York, 1990; pp. 17.
Issa, R. M.; El-Sonbati, A. Z.; El-Bindary, A. A.; Kera, H. M. J. Inorg. Organomet. Polym. 2003, 13, 269-283.
Rivas, B.; Martínez, E.; Pereira, E.; Geckeler, K. E. Polym. Int., 2001, 50, 456-462.
Haddad, P. R.; Jackson, P. E. Ion Chromatography: Principles and Applications; Elsevier: New York; 1990.
Viklund, C.; Irgum, K. Macromolecules 2000, 33, 2539-2544.
Paull, B.; Riordain, C. O.; Nesterenko, P. N. Chem. Commun. 2005, 2, 215-217.
Guo, D.; Mant, C. T.; Taneja, A. K.; Parker, J. M. R.; Hodges, R. S. J. Chromatogr. 1986, 359, 499-517.

* cited by examiner

MONOLITHIC COLUMN TECHNOLOGY FOR LIQUID CHROMATOGRAPHY

CROSS REFERENCE TO RELATED APPLICATIONS

This application claims priority from U.S. Provisional Patent Application 60/683,063, filed 20 May 2005, which is hereby incorporated by reference.

FEDERAL RESEARCH STATEMENT

This invention was made with support from United States Government, and the United States Government has certain rights in this invention pursuant to National Institutes of Health contract number R01 GM 64547-01A1.

BACKGROUND OF INVENTION

Minimal interaction of support matrix and analytes is often desirable for separations such as gel electrophoresis and size exclusion chromatography of proteins. Proteins are well known to exhibit hydrophobic and/or ionic interactions with a variety of surfaces. Therefore, an inert material, which can significantly reduce or eliminate adsorption of proteins, would be very useful.

Known materials that resist protein adsorption include polysaccharide and polyacrylamide polymers; these enjoy wide application in gel electrophoresis and size exclusion separation of proteins[1]. An efficient method to address adsorption problems in capillary electrophoresis is to coat the capillary surface with such polymers[2,3]. In addition to polysaccharide and polyacrylamide, other neutral hydrophilic polymers have been investigated and found useful in capillary electrophoresis, such as polyvinyl alcohol[4], polyethylene oxide[5,6], polyvinylpyrrolidinone[7] and a copolymer of polyethylene glycol and polypropylene glycol[8]. All of these polymers are neutral and hydrophilic. A systematic study of protein adsorption with a variety of surface structures resulted in the conclusion that materials are protein compatible if they are neutral, hydrophilic, proton acceptors and not proton donors[9-11].

Other materials used in gel electrophoresis reported in 1992 by Zewert and Harrington are polyhydroxy methacrylate, polyhydroxy acrylate, polyethylene glycol methacrylate and polyethylene glycol acrylate[12,13]. To avoid the toxicities of acrylamide and bisacrylamide, and the difficulties associated with polyacrylamide gel electrophoresis of very hydrophobic proteins, such as bovine serum albumin or zein, polyethylene glycol methacrylate 200 in hydroorganic solvents was evaluated. Although there was no direct evidence to show the inertness of this material, successful electrophoresis of proteins demonstrated the protein compatibility of such polymers.

The inert polymers mentioned above are polymer gels that are soft in nature. These polymers can only be used in their swollen states because such polymers lose their permeabilities upon drying. Attempts have been made to prepare rigid beads with permanent porous structures from such polymers. Among these hydrophilic polymers, polyacrylamide is the only one that can form rigid beads by inverse suspension techniques using a high content of bisacrylamide as a crosslinker[14]. The use of a higher level of crosslinker accounts for the formation of rigid beads instead of soft particles.

Monolithic materials offer an alternative to columns packed with small particles or beads. A monolith (originally called a continuous bed or continuous polymer bed[15]) is a continuous rod with canal-like large through-pores and nanometer-sized pores in the skeletal structure. Preparation of a monolith is typically performed in a mold, such as in a tube or capillary where only one phase of the monomer mixture is used. Two types of monolithic materials have been developed to date. The first type is based on a silica backbone[16,17] in which a continuous sol-gel network can be created by the gelation of a sol solution within a mold. Silica monoliths are mainly used for the separation of small molecules because of their hydrophobic characteristics after derivatization.

The second category includes polymer monoliths[15,18] normally prepared by in-situ polymerization of monomer solutions, which are composed of a monomer, crosslinker, porogen and initiator. They can be initiated either by a redox system, e.g., TEMED and APS, or by a free radical initiator. For free radical initiation, both thermally and, more importantly, UV-initiated polymerization can be used. By the use of UV-initiated polymerization, a spatially defined monolith in a capillary or microchip can be prepared using a suitable mask. Furthermore, UV-initiated polymerization is typically much faster than thermally-initiated polymerization.

The first demonstration of a polyacrylamide monolith was performed in 1989 by Hjertén's group[15]. Acrylic acid and N,N'-methylenebisacrylamide were used as monomer and crosslinker, respectively, to prepare a macroporous gel plug for cation-exchange chromatography of proteins. Favorable chromatographic behavior (i.e., high efficiency at high mobile phase flow rate) was observed although the polymer monolith was compressible.

The preparation of a rigid polyacrylamide-co-bisacrylamide monolith was performed in 1997 by Svec's group[19]. Several variables were studied to prepare a flow-through monolith with a mean pore diameter of ~1 µm. The porogens used for preparing the acrylamide-co-bisacrylamide monolith were dimethyl sulfoxide and a long chain alcohol, such as heptanol or dodecanol. The concentration of initiator was also investigated to adjust the medium pore diameter of the monolith; a lower concentration of initiator increased the permeability of the resulting monolith as expected. Unfortunately, thermally initiated polymerization was used to prepare the monolith. As a result, 24 h was required to complete the polymerization at 1% initiator concentration.

TABLE A

Cited References

1. C. J. R. Morris, P. Morris, Separation Methods in Biochemistry. Wiley, New York, 1976, p. 413-470.
2. S. Hjerten, M. J. Zhu, J. Chromatogr. 346 (1985) 265.
3. S. Hjerten, J. Chromatogr. 347 (1985) 191.
4. N. J. Clarke, A. J. Tomlinson, G. Schomburg, S. Naylor, Anal. Chem. 69 (1997) 2786.

TABLE A-continued

Cited References

5. N. Iki, E. S. Yeung, J. Chromatogr A 731 (1996) 273.
6. J. Preisler, E. S. Yeung, Anal. Chem. 68 (1996) 2885.
7. R. McCormick, Anal. Chem. 60 (1988) 2322.
8. Z. Zhao, A. Malik, M. L. Lee, Anal. Chem. 65 (1993) 2747.
9. R. G. Chapman, E. Ostuni, M. N. Liang, G. Meluleni, E. Kim, L. Yan, G. Pier, H. S. Warren, G. M. Whitesides, Langmuir 17 (2001) 1225.
10. E. Ostuni, R. G. Chapman, R. E., Holmlin, S. Takayama, G. M. Whitesides, Langmuir 17 (2001) 5605.
11. E. Ostuni, R. G. Chapman, M. N. Liang, G. Meluleni, G. Pier, D. E. Ingber, G. M. Whitesides, Langmuir 17 (2001) 6336.
12. T. Zewert, M. Harrington, Electrophoresis 13 (1992) 817.
13. T. Zewert, M. Harrington, Electrophoresis 13 (1992) 824.
14. J. V. Darkins, N. P. Gabbott, Polymer 22 (1981) 291.
15. S. Hjertén, J. L. Liao, R. Zhang, J. Chromatogr. 473 (1989) 273.
16. S. M. Fields, Anal. Chem. 68 (1996) 2709.
17. H. Minakuchi, K. Nakanishi, N. Soga, N. Ishizuka, N. Tanaka, Anal. Chem. 68 (1996) 3498.
18. F. Svec, J. M. J. Fréchet, Anal. Chem. 54 (1992) 820.
19. S, Xie, F. Svec, J. M. J, Fréchet, J. Polym. Sci. A: Polym. Chem. 35 (1997) 1013.
20. C. Yu, M. H. Davey, F. Svec, J. M. J. Fréchet, Anal. Chem. 73 (2001) 5088
21. P. H. Humble, R. T. Kelly, A. T. Woolley, H. D. Tolley, M. L. Lee, Anal. Chem. 76 (2004) 5641.
22. C. Yu, M. Xu, F. Svec, J. M. J. Fréchet, J. Polym. Sci. A: Polym. Chem. 40 (2002) 755.
23. D. S. Peterson, T. Rohr, F. Svec, J. M. J. Fréchet, Anal. Chem. 74 (2002) 4081.
24. J. J. Meyers, A. I. Liapis, J. Chromatogr. A 852 (1999) 3.
25. A. I. Liapis, J. J. Meyers, O. K. Crosser, J. Chromatogr. A 865 (1999) 13.
26. F. Nevejans, M. Verzele, J. Chromatogr. 350 (1985) 145.
27. C. T. Mant, R. S. Hodges (Editors), High-Performance Liquid Chromatography of Peptides and Proteins: Separation, Analysis, and Conformation. CRC Press, Boca Raton, FL, 1991, p. 139-142.
28. G. Szabo, K. Offenmuller, E. Csato, Anal. Chem. 60 (1988) 213.
29. S. Lubbad, M. R. Buchmeiser, Macromol. Rapid Commun. 23 (2002) 617.
30. I. Halasz, K. Martin, Angwew. Chem. (Int. Ed. Engl.) 17 (1978) 901.
31. M. Al-Bokari, D. Cherrak, G. Guiochon, J. Chromatogr. A 975 (2002) 275.
32. D. E. Schmidt, R. Glese, D. Conron, B. Karger, Anal. Chem. 52 (1980) 177.
33. J. K. Towns, F. E. Regnier, Anal. Chem. 63 (1991) 1126.
34. K. K. C. Yeung, C. A. Lucy, Anal. Chem. 69 (1997) 3435.
35. J. Cunliffe, N. E. Baryla, C. A. Lucy, Anal. Chem. 74 (2002) 776.
36. C. T. Culbertson, J. W. Jorgenson, Anal. Chem. 66 (1994) 955.
37. D. G. McLaren, D. D. Chen, Electrophoresis, 24 (2003) 2887.
38. Kimura, H.; Tanigawi, T.; Morisaka, H.; Ikegami, T.; Hosoya, K.; Ishizuka, N.; Minakuchi, H.; Nakanishi, K.; Ueda, M.; Cabrera, K.; Tanaka, N. J. Sep. Sci. 2004, 27, 897-904.
39. Gu, B; Armenta, J. M.; Lee, M. L. J. Chromatogr. A 2005, 1079, 382-391.
40. Guyot, A.; Bartholin, M. Prog. Polym. Sci. 1982, 8, 277-332.
41. Sederel, W. L.; Jong, G. J. J. Appl. Polym. Sci. 1973, 17, 2835-2846.
42. Kun, K. A.; Kunin, R. J. Polym. Sci.: Part A1 1968, 6, 2689-2701.
43. Svec, F. LC-GC, Europe 2003, 16(6a), 24-28.
44. Svec, F. J. Sep. Sci. 2004, 27, 747-766.
45. Svec, F. J. Sep. Sci. 2004, 27, 1419-1430.
46. Burke, T. W. L.; Mant, C. T.; Black, J. A.; Hodges, R. S. J. Chromatogr. 1989, 476, 377-389.
47. Mant, C. T.; Hodges, R. S. In High-Performance Liquid Chromatography of Peptides and Proteins: Separation, Analysis, and Conformation; Mant, C. T.; Hodges, R. S., Ed.; CRC Press: Boca Raton, 1991; pp 171-185.
48. Alpert, A. J.; Andrews, P. C. J. Chromatogr. 1988, 443, 85-96.
49. Imamura, T.; Sugihara, J.; Yokata, E.; Kagimoto, M.; Naito, Y.; Yanase, T. J. Chromatogr. 1984, 305, 456-460.
50. Kawasaki, H.; Imajoh, S.; Suzuki, K. J. Biochem. 1987, 102, 393-400.
51. Stadalius, A. A.; Quarry, M. A.; Snyder, L. R. J. Chromatogr. 1985, 327, 93-113.
52. Mant, C. T.; Hodges, R. S. In High-Performance Liquid Chromatography of Biological Macromolecules: Methods and Applications; Gooding, K.; Regnier, F., Eds.; Marcel Dekker: New York, 1990; pp 301-332.

TABLE A-continued

Cited References

53. Mant, C. T.; Hodges, R. S. J. Chromatogr. 1985, 326, 349-356.
54. Mant, C. T.; Hodges, R. S. J. Chromatogr. 1985, 327, 147-155.
55. Crimmins, D. L.; Thoma, R. S.; McCourt, D. W.; Schwartz, B. D. Anal. Biochem. 1989, 176, 255-260.
56. Crimmins, D. L.; Gorka, J.; Thoma, R. S.; Schwartz, B. D. J. Chromatogr. 1988, 443, 63-71.
57. Viklund, C.; Svec, F.; Fréchet, J. M. J. Biotechnol. Prog. 1997, 13, 597-600.
58. Ueki, Y.; Umemura, T.; Li, J.; Odake, T.; Tsunoda, K. Anal. Chem. 2004, 76, 7007-7012.
59. Zakaria, P.; Hutchinson, J. P.; Avdalovic, N.; Liu, Y.; Haddad, P. R. Anal. Chem. 2005, 77, 417-423.
60. Hilder, E. F.; Svec, F.; Fréchet, J. M. J. J. Chromatogr. A 2004, 1053, 101-106.
61. Righetti, P. G. in Immobilized pH Gradients. Theory and Methodology; Burdon, R. H.; van Knippenberg, P. H., Eds.; Elsevier: New York, 1990; pp 17.
62. Issa, R. M.; El-Sonbati, A. Z.; El-Bindary, A. A.; Kera, H. M. J. Inorg. Organomet. Polym. 2003, 13, 269-283.
63. Rivas, B.; Martinez, E.; Pereira, E.; Geckeler, K. E. Polym. Int., 2001, 50, 456-462.
64. Haddad, P. R.; Jackson, P. E. Ion Chromatography: Principles and Applications; Elsevier: New York; 1990.
65. Viklund, C.; Irgum, K. Macromolecules 2000, 33, 2539-2544.
66. Paull, B.; Riordain, C. O.; Nesterenko, P. N. Chem. Commun. 2005, 2, 215-217.
67. Guo, D.; Mant, C. T.; Taneja, A. K.; Parker, J. M. R.; Hodges, R. S. J. Chromatogr. 1986, 359, 499-517.

SUMMARY OF INVENTION

The present invention involves a monolith containing macropores allowing flow of solvent and analyte. The monolith comprises a backbone that provides structural integrity to the monolith contains mesopores for a high-surface contact area for analyte interaction. The backbone itself is essentially non-adsorptive to proteins, peptides, and like substances. There are functional groups on the surface that provide a chemistry of interaction. However, the composition of the support matrix, except for any of these functional groups on its surface, is hydrophilic and nonadsorptive to proteins. Accordingly, with the non-adsorptive backbone, the backbone presents minimal specific or non-specific interactions that interfere or compete with the interaction of functional groups. Hydrophobic, highly hydrophilic and otherwise protein interactive surfaces on the backbone or support matrix are minimized so that any nonspecific interactions with analytes are minimized.

Because the backbone is essentially non-adsorptive, the desired interaction designed for the monolith can dominate. Such interactions can be interactions with functional groups on the surface or size specific interactions with micropores, and mesopores. The result approaches a single mode, rather than a mixed mode separation that results when there are multiple competing interactions. This allows for a separation that is of high-efficiency and with narrow peaks that are symmetrical, i.e., lacking any tail.

The monolith is produced by the copolymerization of a (1) monomer having a reactive vinyl group, and (2) a crosslinker having at least two vinyl reactive groups and a backbone comprising poly(ethylene oxide) (PEO) or poly(propylene oxide) (—CH(CH$_3$)CH$_2$O—, —CH$_2$CH$_2$CH$_2$O—) (PPO) or a mixed polymer of ethylene oxide (EO) and propylene oxide (PO), i.e., poly(ethylene-propylene oxide) (PEPO). The selection of the monomer depends upon the desired mode of separation, and the sort of interactivity that the monomer will impart to the monolith surface.

The reaction to produce the monolith may be any suitable reaction, but is preferable polymerization by free-radical reaction between vinyl groups. The reaction is preferably UV initiated because of ease and rapidity of the reaction. However, other reaction schemes (e.g. thermally initiated, catalyst) are suitable. To form flow through pores for analyte in the monolith a suitable porogen is added to the reaction mixture.

Crosslinker

As described above, the crosslinker has a backbone comprising a PEO, PPO, or PEPO, and has end groups having a vinyl group that can participate in the polymerization reaction.

An exemplary crosslinker with 2 vinyl groups can be depicted as:

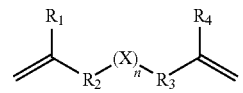

where n is equal to or greater than 3,

X is —CH$_2$CH$_2$O—, or —CH(CH$_3$)CH$_2$O—, or —CH$_2$CH$_2$CH$_2$O—, or a mixture thereof, R$_1$ and R$_4$ are the same or different and are —H, or —CH$_3$, R$_2$ is selected from the group consisting of

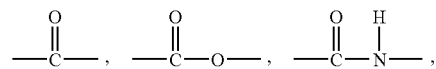

—O—, or is nothing, and $R_3$ is selected from the group consisting of

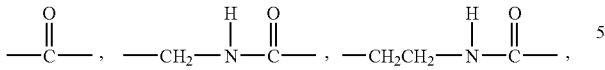

—$CH_2CH_2$—, or is nothing.

Another example of a class of crosslinkers with two vinyl groups can be described as follows;

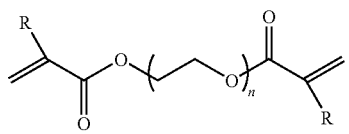

where R is $CH_3$ or H, and n is equal to or greater than 3.

Yet another example can be described as follows:

where n is equal to or greater than 3.

The upper limit of n in the above examples is found where the length of the PEO/PPO chain becomes so large that the monomer cannot form a rigid monolith structure. In addition, with long chains, the cross-linking density is smaller. In general, it is believed that cross-linkers with n between 3 and 20 are suitable.

The crosslinker can also have more than two vinyl groups. Exemplary crosslinker compounds in this class are as follows;

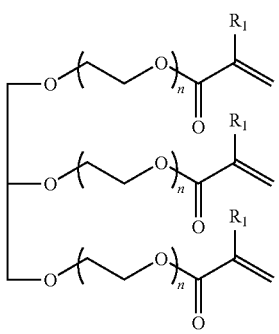

where in each chain n is the same or different and is at least 1, $R_1$ in each pendant group is the same or different and is H, or $CH_3$.

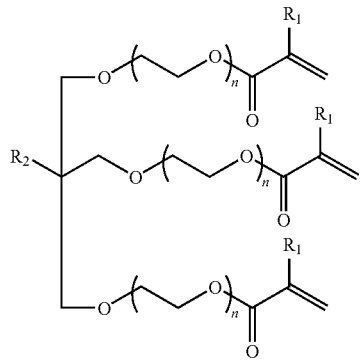

where in each chain n is the same or different and is at least 1, $R_1$ in each pendant group is the same or different and is H, or $CH_3$, and $R_2$ is $CH_2OH$ or another hydrophilic group, such as a group including PPO or PEO and, optionally terminating with a vinyl group, or $CH_2CH_3$.

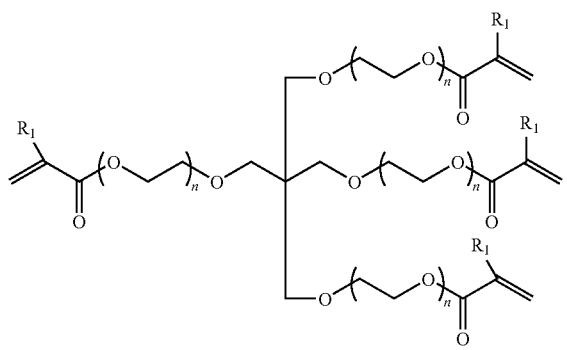

where n is at least 1 and the same or different in each chain, and $R_1$ in each chain is the same or different and is H, or $CH_3$.

In any of the above formulas, a propylene oxide group can be substituted for an ethylene oxide group. Likewise, an ethylene oxide group can be substituted for a propylene oxide group. Below are further examples that illustrate crosslinkers with mixed propylene oxide and ethylene oxide chains. In each example n and m are the same or different and are 0 or greater, and n+m is 3 or more. The formulas are not intended to show the ethylene oxide and propylene oxide groups as joined only in blocks, but also to show the respective number, n and m, of EO and propylene oxide PO groups, which can occur in the chain in any order. Thus, for example, $-(EO)_2-(PO)_3-$ is a representation of several structures, including -EO-PO-PO-PO-, -EO-E-PO-EO-PO-PO-, and -EO-PO-PO-PO-EO-.

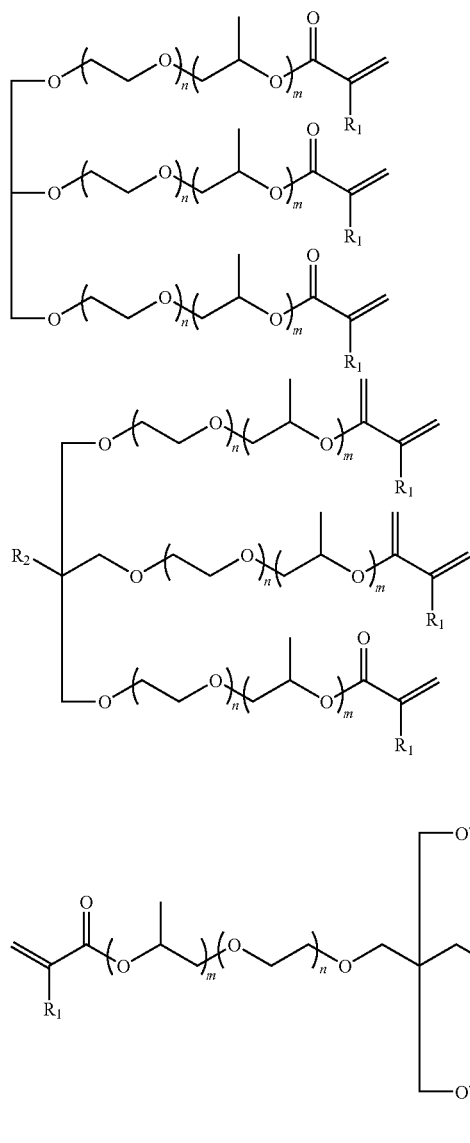

In general, the crosslinker can be described as a compound having a backbone with at least three adjacent X groups, where X is ethylene oxide or propylene oxide or a mixture thereof, and two or more pendant vinyl groups (—CH=CH$_2$).

There may be groups between the ethylene oxide or propylene oxide groups and the vinyl end groups, such those depicted above. These include any suitable group that does not materially participate in or compete with the polymerization reaction to form the monolith, or the selectivity of the functional groups on the monolith surface. As a guideline, but not a limitation, in the pendant group (that which includes the vinyl reaction site and is bonded to a propylene oxide or ethylene oxide) there are typically no more than 5 carbons.

Because of availability and ease of formation, acrylate or methacrylate end groups are preferred. A suitable and readily available crosslinker is poly(ethylene glycol) diacrylate (PEGDA), or poly(ethylene glycol) dimethacrylate. However, as noted above the acrylate or methacrylate group can be replaced by a —CH=CH$_3$ or —C(CH$_3$)=C group, as all that is required from the pendant end group is a reactive vinyl group. The crosslinker may comprise only one compound from any of the suitable structures described above, or may comprise a mixture of two or more crosslinker compounds. For example, by varying the ratio between crosslinker with respective short and long PEO or PPO chains, the flexibility and other structural properties of the monolith end product may be controlled.

Monomer

The monomer is any suitable compound that has a desired functional group and a vinyl group that is sufficiently reactive to participate in the polymerization reaction to form the monolith. The functional group is selected, based upon the type of chromatographic separation that is desired, i.e., the property of the analyte used to effect separation.

The monolith of the invention can be made for use in any liquid chromatography separation system that functions by interactions between a monolith and target analytes.

The monomer can be described by the formula;

$$CH_2=CR—Y—Z$$

where Z is a functional group selected to impart a desired interaction property to the monolith, and R is H or $CH_3$.

Below in Table B are shown various liquid chromatography systems and the target analytes for separation with which the monolith is designed to have interactive properties, and the type of functional group, Z, that would be chosen for that particular system.

TABLE B

LC Systems and Functional Groups

| Liquid Chromatography System | Target Analytes - Property used to effect separation | Functional Group, Z |
|---|---|---|
| Ion Exchange | Molecules with different ionic charges, ions | Cations or Anions |
| Chiral | Enantiomers | Chiral Selectors |
| Reversed-Phase | All types based upon hydrophobic/hydrophilic character | Hydrophobic alkyl chains, $—(CH_2)_n—CH_3$, where n = 3-17 |
| Hydrophobic Interaction | Primarily proteins based upon hydrophobic patches in molecule | Hydrophobic alkyl chains, $—(CH_2)_n—CH_3$, where n = 1-7, and phenyl |
| Size Exclusion | Large Molecules based on size | Not interactive with analyte to allow interaction with meso- and micropores, $—CH_3$ and —H |

The intervening group Y, is nothing, or any group that will not materially affect or compete with the function of the functional group (Z) in the monolith, or the reactivity of the vinyl group ($CH_2=CH—$) in the polymerization reaction to form the monolith. For most applications where the analytes are proteins or protein-like compounds, examples of Y can include one or more of $—CH_2—$, $—CO—$, $—NH—$, $—C(CH_3)_2—$, $—(CH_2CH_2O)_n—$, $—(CH(CH_3)CH_2O))_n—$, $—O—$ or any other suitable group. The Y groups should have an essentially non-interactive character toward the analytes, i.e., not hydrophobic and not excessively hydrophilic.

Formation of the Monolith

The monolith is formed by first providing a liquid reaction mixture of crosslinker and monomer. Other materials are also added as required. For example a porogen is also added in sufficient amount to form a porous, i.e., flow through, matrix of the crosslinker/monomer reaction product. Preferably the reaction is free-radical initiated, using a UV initiator, which is also added to the reaction mixture. Typically the mixture will have 20 to 80 weight percent of cross-linker, based upon the combined weights of cross-linker and monomer.

The reaction mixture is subjected to the conditions to initiate polymerization reaction between the crosslinker and the monomer. The porogen may be any suitable liquid material, and for any system the nature of the porogen and its quantity in the mixture can be determined by routine experimentation. Porogens containing one or more of water, methanol and ethyl ether have been found suitable.

The monolith resulting from the reaction comprises a supporting structure or matrix with a backbone that is essentially non-adsorptive to proteins, due to the preponderance of PEO, PPO, and PEPO in its composition, with functional groups attached to the surface. This is achieved by reacting a monomer that has the functional groups with a cross-linking agent that does not introduce a protein incompatible structure to the supporting matrix. The present invention solves the problem of significant non-specificity by manufacture of a monolith that has active sites supported by a matrix that is essentially non-adsorptive, particularly to proteins and like substances.

Examples of Monomers for Ion Exchange Liquid Chromatography

For ion exchange liquid chromatography, the Z group is a cationic or anionic group. Cation exchange groups include sulfonate ($—SO_2OH$), carboxylate ($—COOH$), or phosphate ($—PO(OH)_2$). Anion exchange groups include $—NH_2$, $—NHR_1$, $—NR_1R_2—$, or $NR_1R_2R_3^+$, where $R_1$, $R_2$, and $R_3$ are the same or different and are methyl or ethyl.

Exemplary monomers suitable for ion exchange monoliths include, but are not limited to;

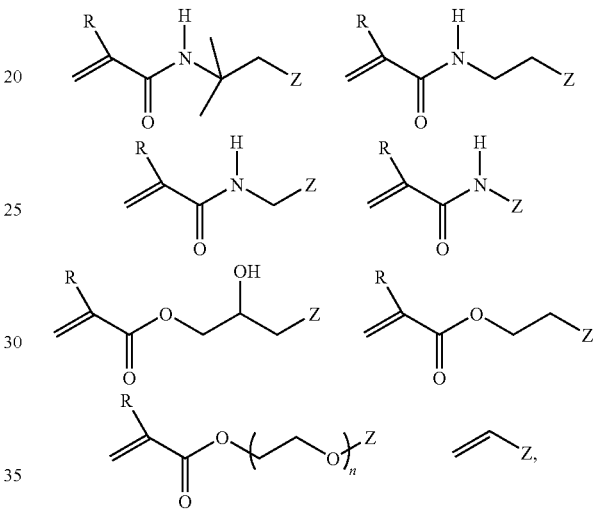

where Z is a cation or an anion. In addition, Z may be any another suitable functional group that is compatible with the structure of the monomer.

Between clusters are through-pores, which determine the permeability of the monolith.

Figure 4:
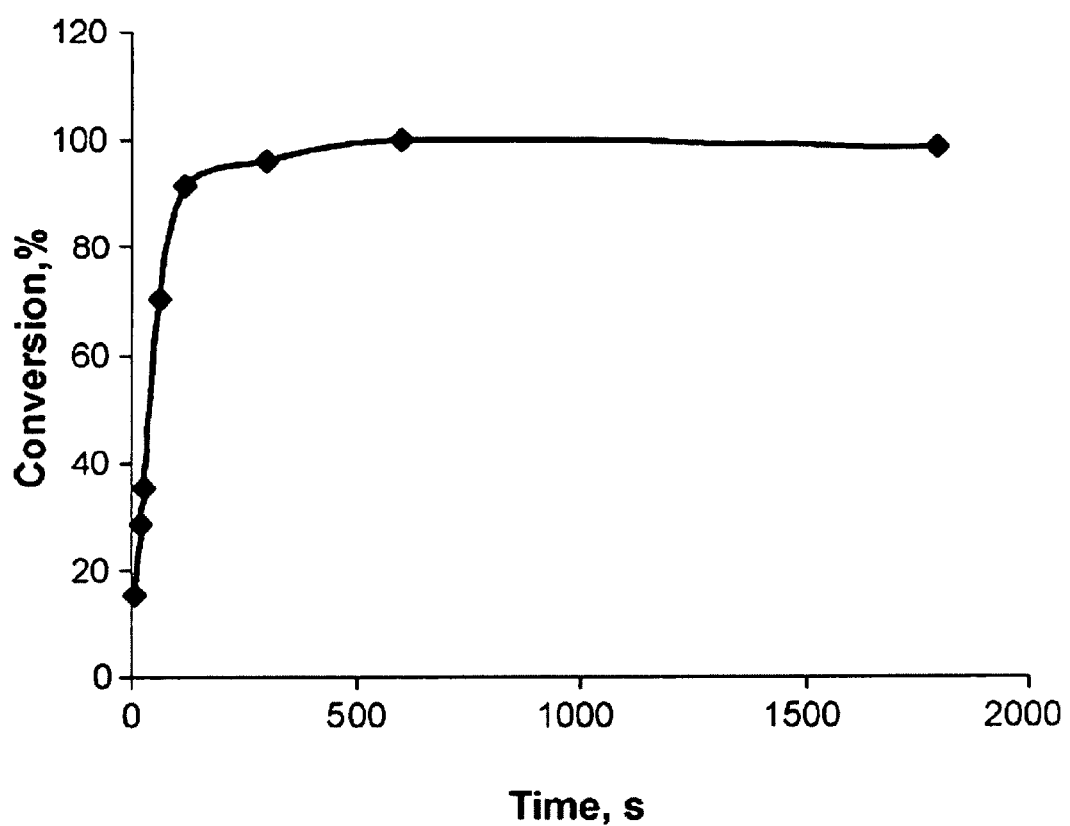

FIG. 4 is a graph showing rate of conversion of monomers to polymer.

Figure 5:
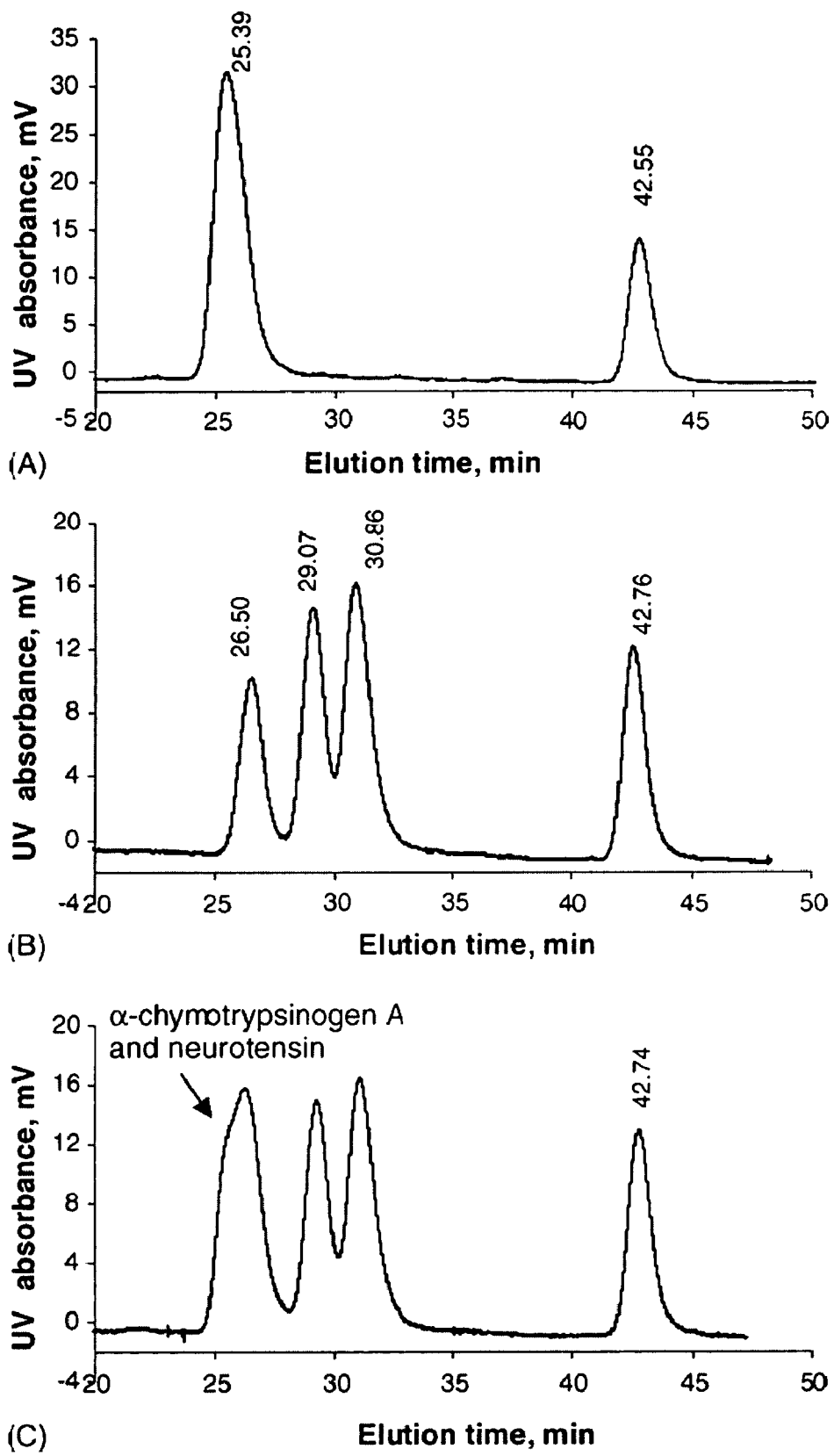

FIG. 5 shows chromatograms of mixtures of several peptides, proteins and thiourea under isocratic elution conditions. The mobile phase was 100 mM phosphate buffer pH 7.0 containing 0.5 M NaCl, operated at a constant pressure of 600 psi (accurate flow rate was not measured). The stationary phase was 75 µm i.d., 60 cm effective length of PEGMEA/PEGDA/monolith. Concentrations were thiourea, 0.15 mg/ml, proteins, 0.8 mg/ml each, and peptides, 0.5 mg/ml each. (A) mixture of bovine serum albumin, pepsin, a-chymotrypsinogen A, myoglobin, lysozyme and thiourea; (B) mixture of neurotensin, angiotensin II fragment 3-8, leucine enkephalin and thiourea (in elution order); (C) mixture of a-chymotrypsinogen A, neurotensin, angiotensin II fragment 3-8, leucine enkephalin and thiourea. For physical properties of the proteins and peptides, see Table D.

Figure 6:
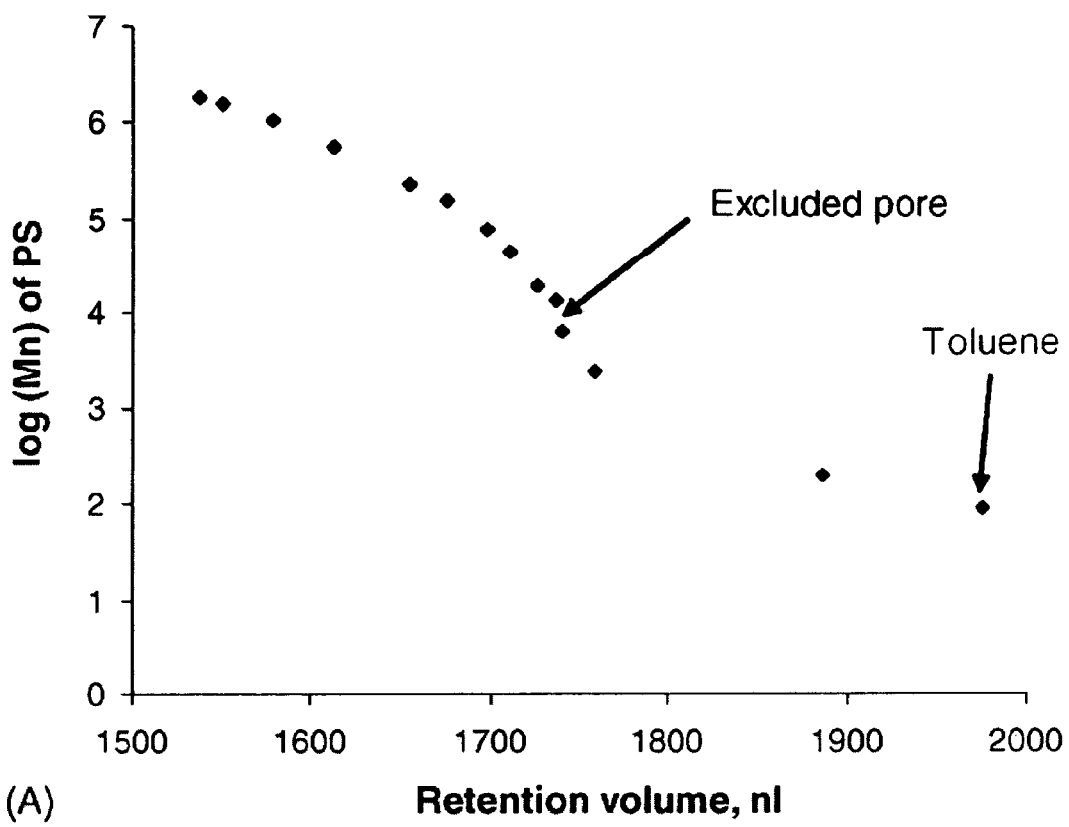
Figure 6:
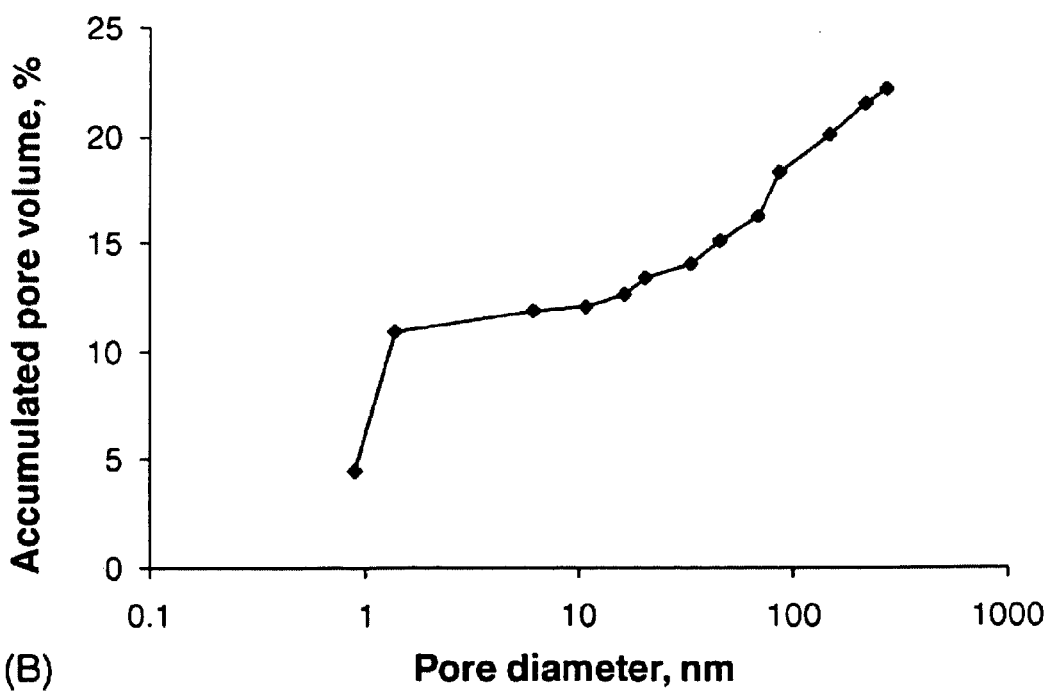

FIG. 6 is a ISEC plot (panel A) and accumulated pore size distribution (panel B) for the PEGMEA/PEGDA monolithic column. THF was used as mobile phase under a constant pressure of 1500 psi, and the mobile phase flow rate was measured to be 0.45 µl/min by monitoring the movement of liquid meniscus in the capillary. A 75 µm i.d., 59.3 cm long monolithic column with online detection at 254 nm was used. In panel A, toluene (Mn 92) was used as a small molecule to determine the total porosity of the column. The exclusion pore volume was approximately the intersection point of the interpolated straight lines corresponding to the internal and external pore zones.

Figure 7:
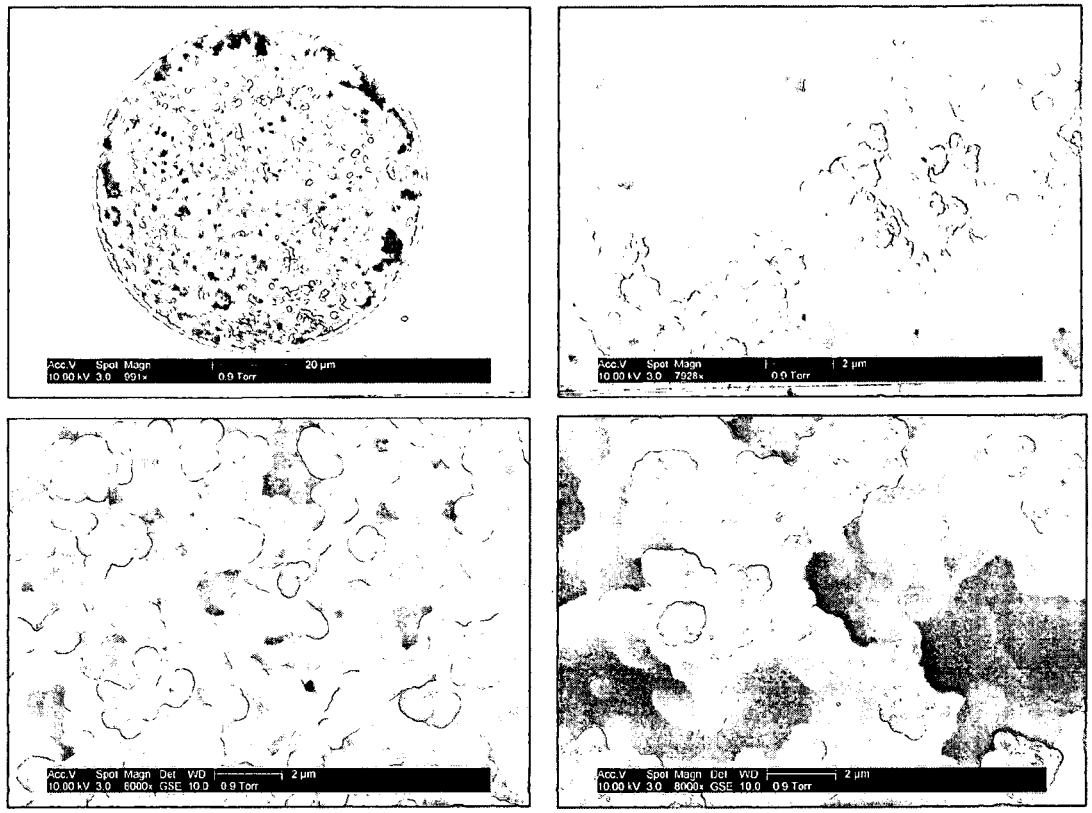

FIG. 7 shows SEM photographs of several synthesized monoliths. (A) optimized poly(AMPS-co-PEGDA) monolith (scale bar=20 mm); (B) higher magnification of the monolith in (A) (scale bar=2 mm); (C) poly(AMPS-co-PEGDA) monolith that has the same composition as (A) except that methanol and ethyl ether were 0.85 and 1.40 g, respectively (scale bar=2 mm); (D) poly(AMPS-co-EDMA) monolith (recipe: 0.008 g DMPA, 0.35 g AMPS, 0.40 g EDMA, 0.35 g water, 1.10 g methanol, scale bar=2 mm).

Figure 8:
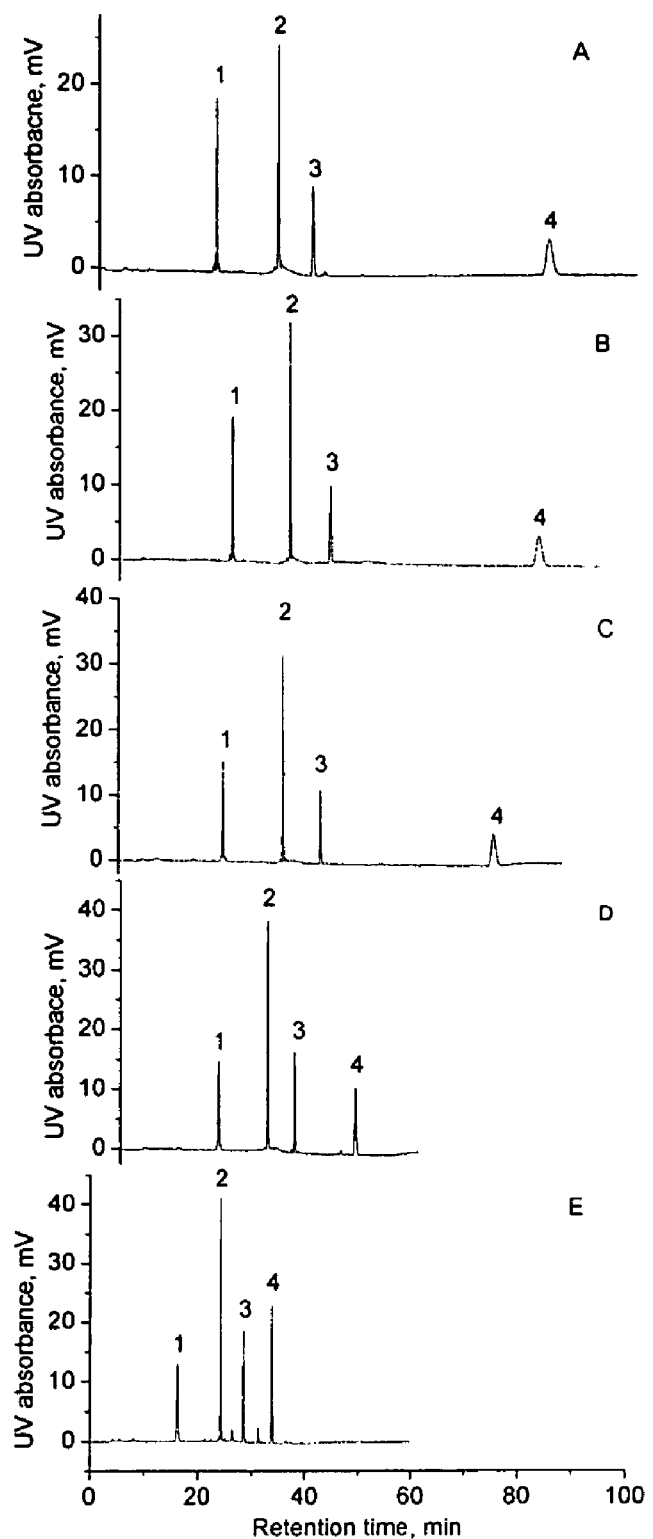

FIG. 8 shows graphs of strong cation exchange (SCX) chromatography of synthetic peptides. Conditions: 16.5 cm×75 mm i.d. monolithic column; buffer A was 5 mM $NaH_2PO_4$ (pH 2.7) and buffer B was buffer A plus 0.5 M NaCl, both buffers containing 0, 10, 20, 30, or 40% (v/v) acetonitrile (panels A, B, C, D, and E, respectively); 2 min isocratic elution of 1% B, followed by a linear AB gradient (5% B/min, equating to 25 mM salt/min) to 100% B and various times of isocratic elution of 100% B until peptide 4 was eluted; ~10 min gradient delay time; mixture of peptides 1-4 (see Table E) for sequence) in CES-P0050, which was dissolved in 400 mL buffer A with 0% acetonitrile, resulting in a concentration of 0.44 mM for peptide 3; 69 mL/min pump master flow rate; 76, 83, 85, 89 or 100 nL/min column flow rates (panels A, B, C, D, and E, respectively); online UV detection at 214 nm.

Figure 9:
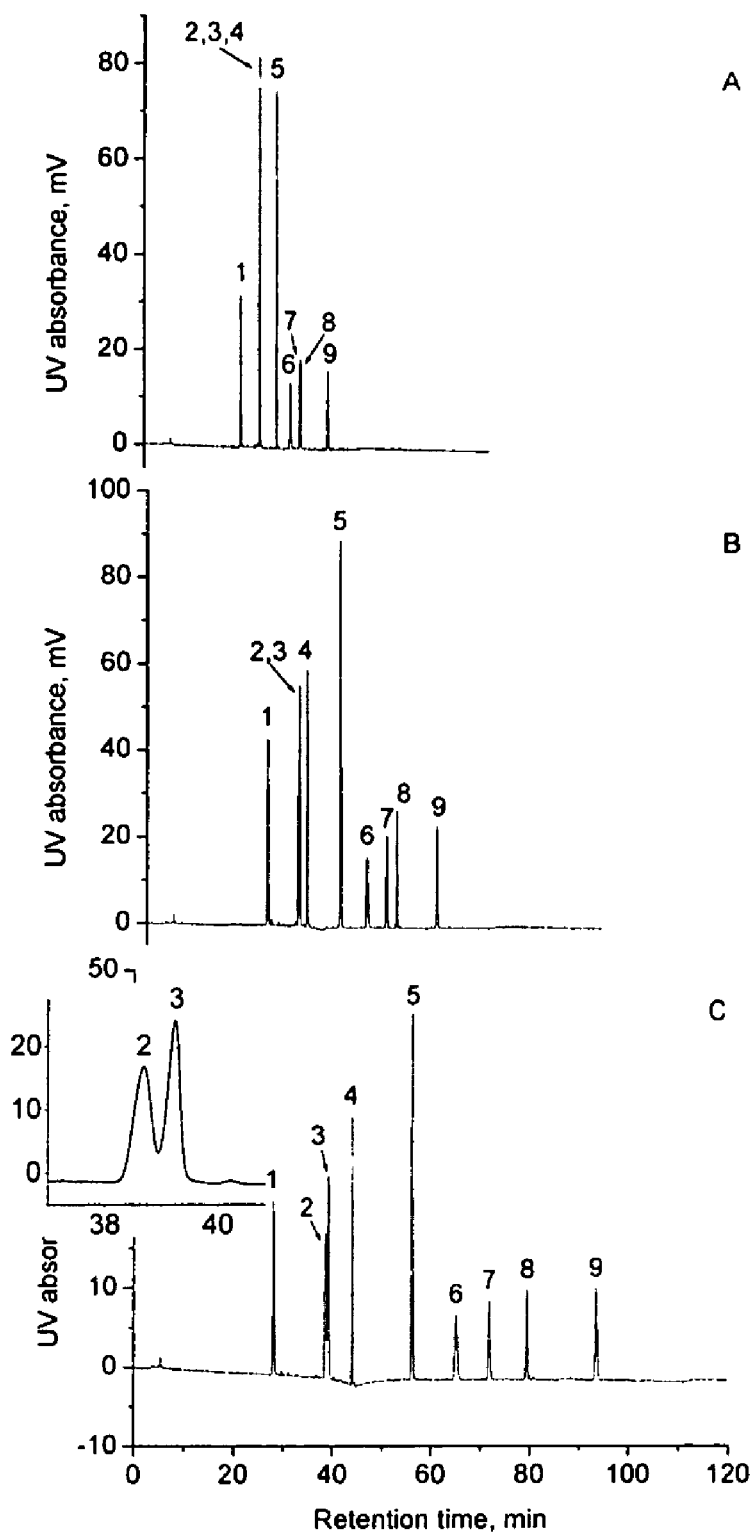

FIG. 9 shows graphs of SCX chromatography of natural peptides. Conditions were the same as those in FIG. 8(E) with the following exceptions: mixture of nine natural peptides (see Table F) dissolved in 25 mL buffer A to make each peptide ~1 mg/mL; gradient rate of (A) 5% B/m in; (B) 2% B/m in; (C) 1% B/m in.

Figure 10:
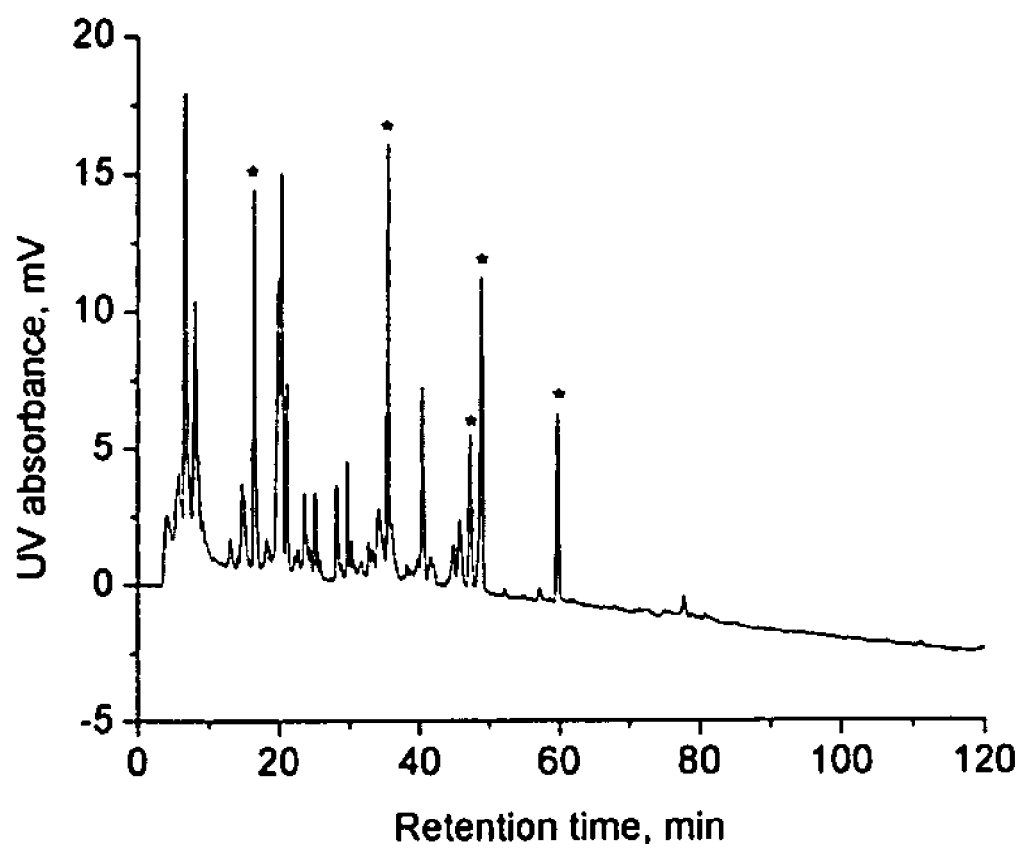

FIG. 10 shows a graph of SCX chromatography of beta-casein digest. Conditions were the same as in FIG. 9(C).

Figure 11:
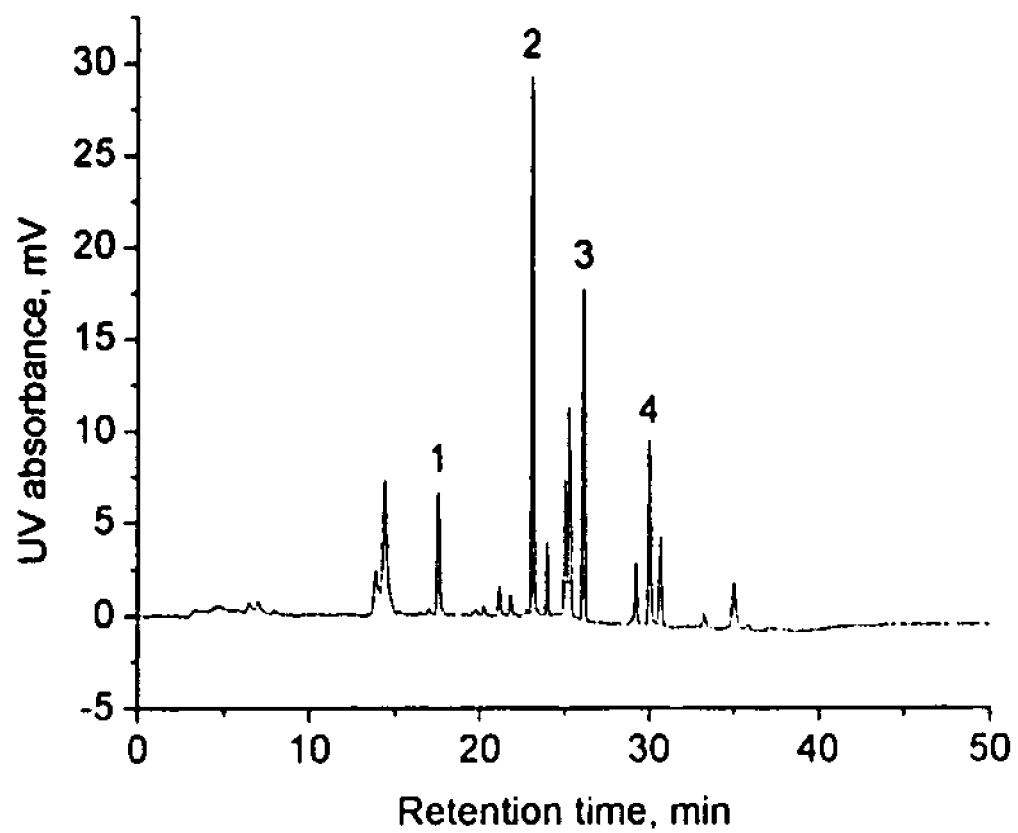

FIG. 11 shows a graph of SCX chromatography of old synthetic peptide sample. Conditions were the same as in FIG. 8(E).

Figure 12:
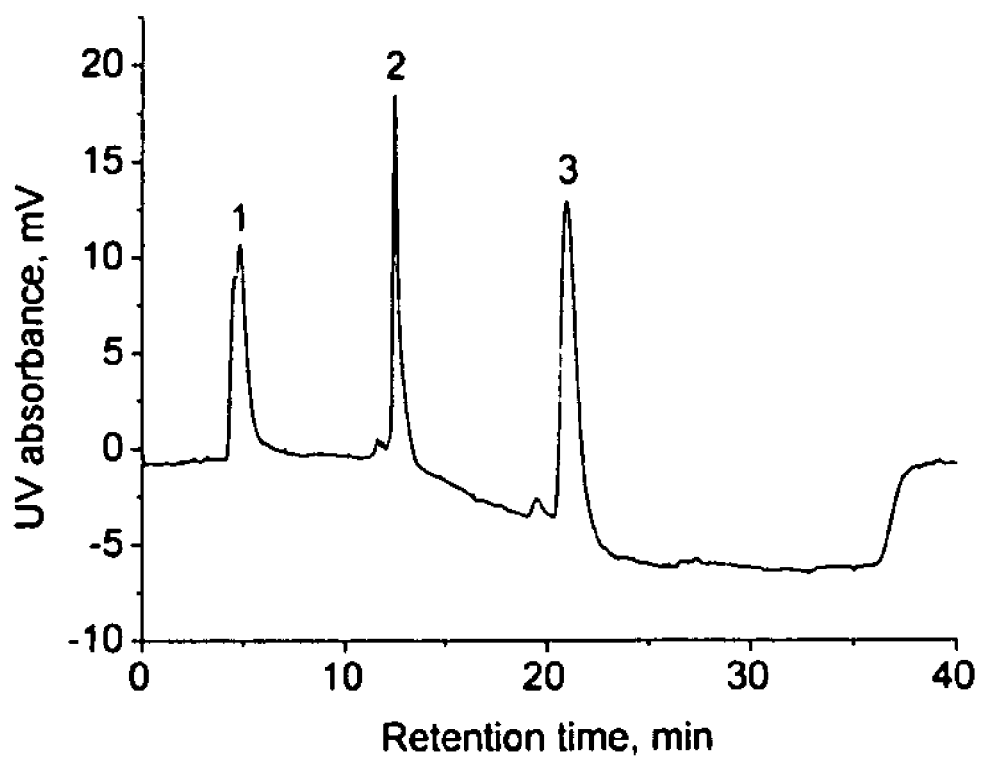

FIG. 12 shows a graph of SCX chromatography of proteins. Conditions were the same as in FIG. 8(E) except that different buffers were used; buffer A was 5 mM phosphate (pH 6.2) and buffer B was buffer A plus 2.0 M NaCl; analytes: (1) myoglobin, (2) cytochrome c, and (3) lysozyme. The baseline drift during gradient elution and the rise of the baseline at the end of gradient were due to the difference in UV absorbances of buffers A and B.

DETAILED DESCRIPTION

Example I

In this example a protein compatible poly(polyethylene glycol methyl ether acrylate-co-polyethylene glycol diacrylate) monolith (PEGMEA/PEGDA) was prepared by photo-initiated polymerization. Physical properties, such as pressure drop and swelling or shrinking in organic solvents, were characterized first, and then inertness in LC was evaluated by using a series of both acidic and basic model proteins under a variety of buffer conditions.

The poly(polyethylene glycol methyl ether acrylate-co-polyethylene glycol diacrylate) monolith was prepared by UV initiated polymerization. Methanol and ethyl ether were selected as porogens from a variety of organic solvents to achieve the desirable characteristics of the monolith. The preparation of the monolith could be achieved within 10 min. The monolith was macroscopically homogeneous, had low flow resistance, and did not swell or shrink significantly in tetrahydrofuran. Inverse size exclusion data indicate that the monolith had a total porosity of 75.4% and an internal porosity of 9.1%. The monolith could be used for size exclusion separation of peptides, although it could not separate proteins with molecular masses between 10~100 K due to its unique pore size distribution, it was found to resist adsorption of proteins in capillary liquid chromatography when using 100 mM phosphate buffer (pH 7.0) containing 0.5 M NaCl. Complete recovery of both acidic and basic proteins was achieved. The monolith can be used for applications in which inert materials are required for protein analysis.

Experimental

Chemicals

Anhydrous methanol, anhydrous ethyl ether and ACS reagent hexanes were purchased from Mallinckrodt Chemicals (Phillipsburg, N.J.), Fisher Scientific (Fair Lawn, N.J.) and EMD Chemicals (Gibbstown, N.J.), respectively. HPLC grade toluene and THF were from Mallinckrodt Chemicals and Curtin Matheson Scientific (Houston, Tex.), respectively. All other solvents (cyclohexanol, dodecanol and dimethyl sulfoxide) were of analytical grade or better. Phosphate buffer solutions were prepared with deionized water from a Millipore water purifier (Molsheim, France) and filtered through a 0.22 µm filter. Thiourea (99.9%), 2,2-dimethoxy-2-phenylacetophenone (99%), 34-trimethoxysilyl)-propyl methacrylate (98%), ethylene dimethacrylate (98%), poly(ethylene glycol) methyl ether acrylate (PEGMEA, average molecular weight, Mn, ~454), and poly(ethylene glycol) diacrylate (PEGDA, Mn ~575 and ~258) were supplied by Sigma-Aldrich (Milwaukee, Wis.) and used without further purification. Proteins [pepsin from porcine stomach mucosa, bovine serum albumin (>99%), myoglobin from horse skeleton muscle, α-chymotrypsinogen A from bovine pancreas, lysozyme from turkey egg white, and bovine serum albumin fluorescein isothiocyanate conjugate (FITC-BSA)] and peptides (neurotensin, angiotensin II fragment 3-8 and leucine enkephalin) were also obtained from Sigma-Aldrich.

Capillary Liquid Chromatography

UV transparent fused silica capillary tubing with 75 μm i.d. and 365 μm o.d. was supplied by Poymicro Technologies (Phoenix, Ariz.). Capillary LC experiments were performed with an ISCO Model 100 DM syringe pump (Lincoln, Nebr.), 60 nL Valco internal sample loop (Houston, Tex.), a Linear Scientific UVis 203 detector (Reno, Nev.) and a Thermo Separations PC 1000 V3.0 software work station (Fremont, Calif.) for data collection and treatment. The PC 1000 provided retention times, peak heights, peak areas, asymmetry factors and column plate counts. On-column UV detection was performed at 214 nm. Chromatograms were transferred to an ASCII file and redrawn using Microsoft Excel (Redmond, Wash.).

Preparation of Polymer Monoliths

Before filling the UV transparent capillary with monomer mixture, the capillary inner surface was treated with 3-(trimethoxysilyl)propyl methacrylate (commercial identification number Z-6030) to ensure covalent bonding of the monolith to the capillary wall[3,20]. Briefly, the capillary was rinsed sequentially with acetone, water, 0.2 M NaOH, water, 0.2 M HCl, water and acetone using a syringe pump for 30 min each at a flow rate of 5 μl/min. The washed capillary was then dried in an oven at 120° C. for 1 h, filled with a 30% Z-6030 acetone solution, sealed with a rubber septum and placed in the dark for 24 h. The vinylized capillary was then washed with acetone at a flow rate of 5 μl/min for 10 min, dried using a stream of nitrogen for 3 h, and sealed with a rubber septum until used.

Four monolith recipes as indicated in Table C were prepared to test protein compatibility. The monomer mixture was prepared in a 1 dram (4 ml) glass vial by admixing in sequence the initiator, monomer, crosslinker and porogens, and ultrasonicating for 5 min before use. Because of the low viscosity of the monomer solution, the introduction of monomer solution into the Uv transparent capillary was facilitated by capillary surface tension. The capillary was then placed under a Dymax 5000AS U curing lamp (Torrington, Conn.) for 10 min. For measurement of polymerization conversion (vide infra), a series of irradiation times was used. The UV curing lamp can produce an irradiation intensity of 200 mW/cm$^2$ in the wavelength range of 320~390 nm.

Laser Induced Fluorescence Imaging of FITC-BSA

Laser induced fluorescence (LIF) imaging of FITC-BSA in a series of capillary columns was performed in a device described elsewhere[21]. Briefly, a 488 nm line from an Ar ion laser was used to excite the sample, and the fluorescence was imaged using a Nikon Coolpix 995 digital camera (Tokyo, Japan).

Pressure Drop Measurements

Pressure drop measurements were performed using a Fisons Phoenix 20 CU HPLC pump (Milano, Italy) in the constant flow mode. Methanol and tetrahydrofuran (THF) were pumped through the monolithic column at flow rates of 4, 6, 8 and 10 μl/min, respectively, and the pressure drop for water was measured at 4 μl/min. After stabilizing, the pump pressure was recorded.

Polymerization Conversion Evaluation and Scanning Electron Microscopy (SEM)

A bulk solution of 10 g optimized monomer mixture (monolith #4, Table C) was prepared based on the procedure outlined in Section 2.3. An aliquot of 0.3 g of the monomer mixture was dispensed into a series of 1 dram (4 ml) glass vials and irradiated under the UV lamp for 10 s, 20 s, 30 s, 1 min, 2 min, 5 min, 10 min, and 30 min, respectively. The bulk monolith was carefully removed by breaking the glass vial, and it was sliced into sections, Soxhlet extracted with methanol overnight and placed in a vacuum oven at 60° C. overnight. The dried monolith material was weighed and compared with the combined weight of the monomer and crosslinker to obtain the conversion of monomer to polymer.

One of the dry monoliths (i.e., with 10 min irradiation time) was also used to obtain the SEM images. The monolith was sputtered with ~20 nm gold, and SEM images were taken using an FEI Philips XL30 ESEM FEG (Hillsboro, Oreg.).

Inverse Size Exclusion Chromatography (ISEC)

The same liquid chromatographic system as described in section 2.2 was used for ISEC. The mobile phase was THF and detection was made at 254 nm. Polystyrene standards with narrow molecular weight distributions and average molecular masses of 201, 2,460, 6,400, 13,200, 19,300, 44,100, 75,700, 151,500, 223,200, 560,900, 1,045,000, 1,571,000 and 1,877,000 were purchased from Scientific Polymer Products (Ontario, N.Y.). Solutions of 1 mg/ml polystyrene and toluene each in THF were prepared.

Protein Recovery Determination

A monolithic column with a total length of 80 cm and effective length of 60 cm was prepared with one detection window at 19 cm and the other at 60 cm from the column inlet. The detection window at 19 cm was created by carefully introducing an air bubble during introduction of the monomer solution. A mixture of protein and thiourea (an internal standard to calibrate any detection window response variation due to different background absorbances of the two detection windows) was injected into the monolithic column. Protein recovery was calculated by comparison of the calibrated protein peak area from the second detection window with that from the first one. The calibrated peak area of a protein was obtained by dividing the protein peak area by that of thiourea from the same detection window.

Results and Discussion

Crosslinker Influence on Inertness of the Monolith

Figure 1:
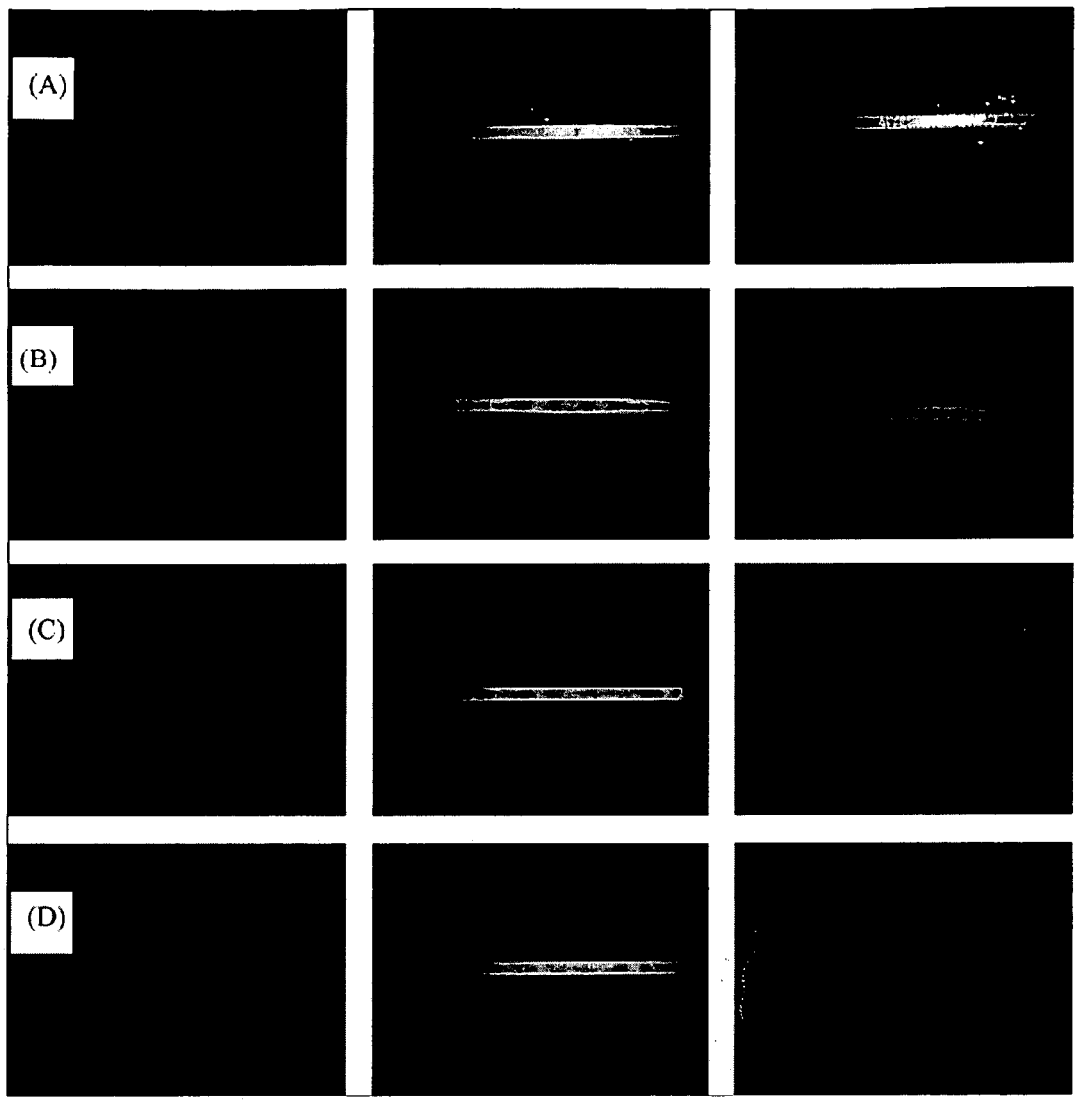
FIG. 1 shows images of the monolith before, during and after loading of FITC-BSA. The LIF image was first recorded before loading of FITC-BSA for which a dark background was obtained for all monoliths. The monolithic column was loaded with 0.01 mg/ml FITC-BSA and the fluorescence image was taken. The monolithic column was then flushed with 100 mM (pH 7.0) phosphate buffer containing 0.5 M NaCl for 5 min under a linear flow velocity of ~4 mm/s, and the LIF image was obtained again. (A) PEGMEA/EDMA monolith, (B) EDMA monolith, (C) PEGDA Mn ~258 monolith and (D) PEGMEA/PEGDA monolith. The monomer recipes for all of the monoliths are listed in Table C.

Initially, ethylene dimethacrylate (EDMA) was chosen as a crosslinker to prepare the PEGMEA monolith because EDMA has been widely used in the preparation of rigid porous polymer monoliths, such as butyl methacrylate, glycidyl methacrylate and hydroxylethyl methacrylate[22]. However, the resultant monolith (monolith #1, Table C) exhibited strong adsorption of FITC-BSA as shown in the LIF images (see FIG. 1, A panels). To investigate the cause of adsorption of BSA in the poly(PEGMEA-co-EDMA) monolith, monolith #2 composed of pure EDMA was prepared with ethyl ether as porogen. Not surprisingly, the EDMA monolith had a strong fluorescence residue after introducing FTIC-BSA and flushing with 0.1 M phosphate buffer (pH 7.0) containing 0.5 M NaCl buffer (FIG. 1, B panels). Because polyethylene glycol is known not to adsorb proteins, polyethylene glycol diacrylate (PEGDA) was chosen as a crosslinker for the preparation of the PEGMEA monolith. Results of the use of PEGDA with Mn ~575 as crosslinker showed that the PEGMEA/PEGDA monolith did resist the adsorption of proteins (data not shown). Unfortunately, the resultant monolith was compressible upon application of >1000 psi buffer even though 75% crosslinker was used in the monomer recipe. This indicates that the PEGMEA monolith with long-chain PEGDA crosslinker yielded a soft monolith. However, replacement of PEGDA Mn ~575 with PEGDA Mn ~258 dramatically improved the rigidity of the monolith. From the fluorescence images (FIG. 1, C panels) of this new polymer monolith #3, no obvious adsorption of FITC-BSA was observed. Therefore, PEGDA Mn ~258 was finally selected as the crosslinker to prepare the PEGMEA/PEGDA monolith (monolith #4, Table C). A fluorescence test of the optimized PEGMEA/PEGDA monolith also showed no adsorption of FITC-BSA (see FIG. 1, panel D).

Optimization of Porogen Composition

To be useful in flow-through applications, the monolith must have low flow resistance. Furthermore, for chromatographic use, a homogeneous monolith is critical for achieving high efficiency. Here, homogeneity refers to the uniformity of the monolithic bed along both radial and axial directions. Because polymer monoliths are made of tiny globules which are connected together to form a continuous rod, they are microscopically heterogeneous. Thus, homogeneity in this example refers to the uniformity of the monolithic bed macroscopically. If the monolith was free of voids or cracks and its color was uniform upon examination under a microscope, the monolith was considered to be homogeneous. Therefore, optimization involved preparing a homogeneous monolith with as low flow resistance as possible.

Five factors can be adjusted to change the pressure drop of the polymer monolith: initiator concentration, total monomer to total porogen ratio, monomer to crosslinker ratio, porogen types and ratio between porogens. Although a decrease in initiator can decrease the pressure drop of the monolith, a longer time is required to complete the polymerization. A decrease in total monomer to total porogen ratio is a straightforward method to decrease the pressure drop of the monolith, however, it decreases the homogeneity and rigidity of the monolith as well. A change in monomer to crosslinker ratio can have an effect on the pressure drop of the resulting monolith, although it also changes the rigidity and homogeneity of the monolith. The most powerful factors to engineer the pressure drop of the monolith are the selection of porogen types and the ratio between porogens, because they do not affect the rigidity of the monolith.

For the preparation of the PEGMEA/PEGDA monolith, when ethyl ether was used as porogen, the crosslinker had to be greater than 70% to make a rigid monolith. As a result, 75% PEGDA (crosslinker) and 25% PEGMEA (monomer) were used throughout the optimization of the monolith. The total monomer to porogen ratio was kept constant at 3:7 and the initiator concentration was 1% of the monomers. A variety of solvents were evaluated to prepare the PEGMEA/PEGDA monolith. First, 30% PEGMEA or PEGDA solutions (containing 1% photoinitiator, 2,2-dimethoxy-2-phenyl-acetophenone, DMPA) in ethyl ether, hexanes, cyclohexanol, dodecanol, dimethyl sulfoxide, methanol, toluene or THF were prepared and placed under the UV lamp to find the potential porogens for the PEGMEA/PEGDA monolith. PEGMEA and PEGDA both dissolved well in all solvents except hexanes. For PEGMEA, dodecanol formed a white solid material, and dimethyl sulfoxide resulted in a transparent soft gel. All other solvents formed a dense liquid after 10 min UV irradiation. For PEGDA, dimethyl sulfoxide and THF resulted in transparent solid materials, which indicate the formation of an extremely small pore structure. All other solvents yielded a white solid, except toluene which formed a yellow rigid solid.

A 2 cm long monolith prepared in a UV transparent capillary was used to test the pressure drop of the monolith composed of only PEGDA. Ethyl ether and methanol porogens yielded a porous monolith, whereas all others would not allow flow at 4500 psi methanol. This is also in contrast to other reported monoliths for which a long-chain alcohol, such as cyclohexanol or dodecanol, was used to prepare a porous monolith[18,19,23]. Therefore, methanol and ethyl ether were selected as porogens to optimize the preparation of the PEGMEA/PEGDA monolith. Since both PEGMEA and PEGDA do not dissolve in hexanes, and both dissolve in mixtures of hexanes and methanol or ethyl ether, hexanes was selected as a macroporogen for the monolith. Thus, the final porogens selected were methanol, ethyl ether and hexanes.

Three porogen mixtures, i.e., methanol/hexanes, ethyl ether/hexanes and methanol/ethyl ether, were optimized for the desired homogeneity and flow resistance of the monolith. The pressure drop of the monolith was found to be insensitive to the ratio of methanol and hexanes or ethyl ether and hexanes. Fortunately, the flow resistance of the monolith was found to be strongly dependent on the ratio of methanol and ethyl ether (see FIG. 2, panel A). For the optimized recipe (monolith #4), i.e., 7.5% PEGMEA, 22.5% PEGDA, 15% methanol and 55% ethyl ether, the pressure drop was 21 psi/(μl/min·cm) when methanol was used as pumping liquid in a 75 μm i.d. monolithic capillary. For a 20 cm×75 μm i.d. capillary, this corresponds to a linear flow velocity of 3.78 mm/s of methanol at a pressure of 420 psi.

Figure 3:
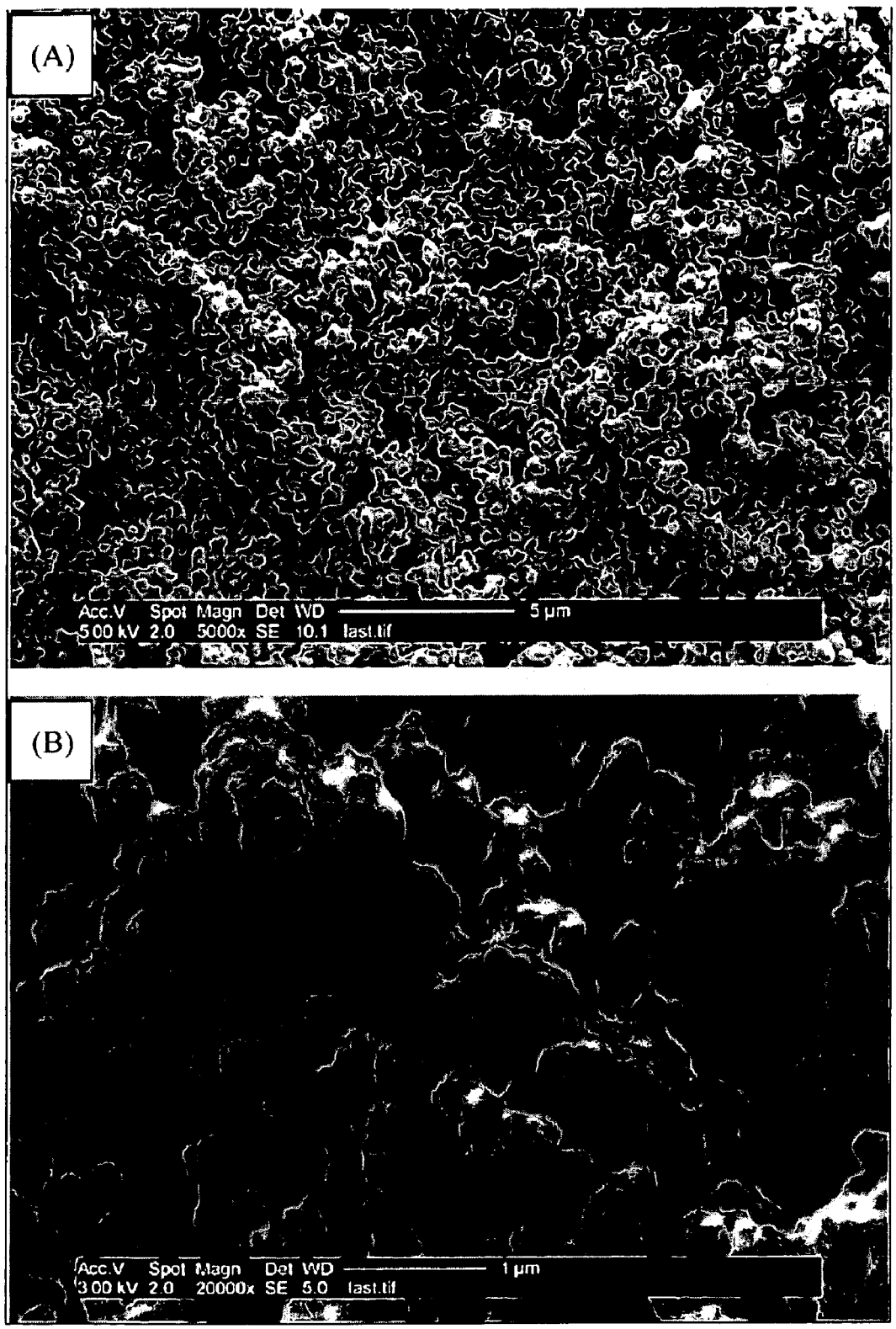
FIG. 3 shows SEM images of the optimized PEGMEA/PEGDA monolith. (A) 5000 magnification, and (B) 20000 magnification. From image B, it is clearly seen that the polymer monolith is composed of microglobules interconnected to form clusters that form the skeleton of the monolith.

SEM images of the optimized PEGMEA/PEGDA monolith are shown in FIG. 3. From the images, a rough estimation of 0.2~0.3 μm diameter globule size could be made. If these globules were tightly packed as in a packed column, the pressure drop would be tremendously high. Therefore, the low flow resistance of 21 psi/(μl/min·cm) was due to the large through-pores or high porosity of the monolith. It may also have been a result of a high degree of connectivity of the through-pores, which has been shown to be a factor affecting the permeability of a monolith in theoretic studies[24,25]. The shrinking of the monolith in methanol (vide infra), could also lead to low flow resistance.

Kinetics of Polymerization of PEGMEA/PEGDA

Both thermal and UV-initiated polymerization can be used to prepare polymer monoliths. Typically, thermally initiated polymerization uses AIBN as initiator, and polymerization proceeds slowly, normally taking 24 h[18,19]. In contrast, photo-initiated polymerization can be finished in minutes[23]. The kinetics of polymerization of PEGMEA/PEGDA is shown in FIG. 4. Over 90% of the monomer was converted into polymer in 2 min, and complete conversion of the monomer was finished in ~10 min. The high irradiation intensity (200 mW/cm$^2$) used in our experiments, which is ~10 fold greater than a previously reported UV curing system[23], contributed to the fast polymerization of the monomer solution.

Physical Properties of the PEGMEA/PEGDA Monolith

Figure 2:
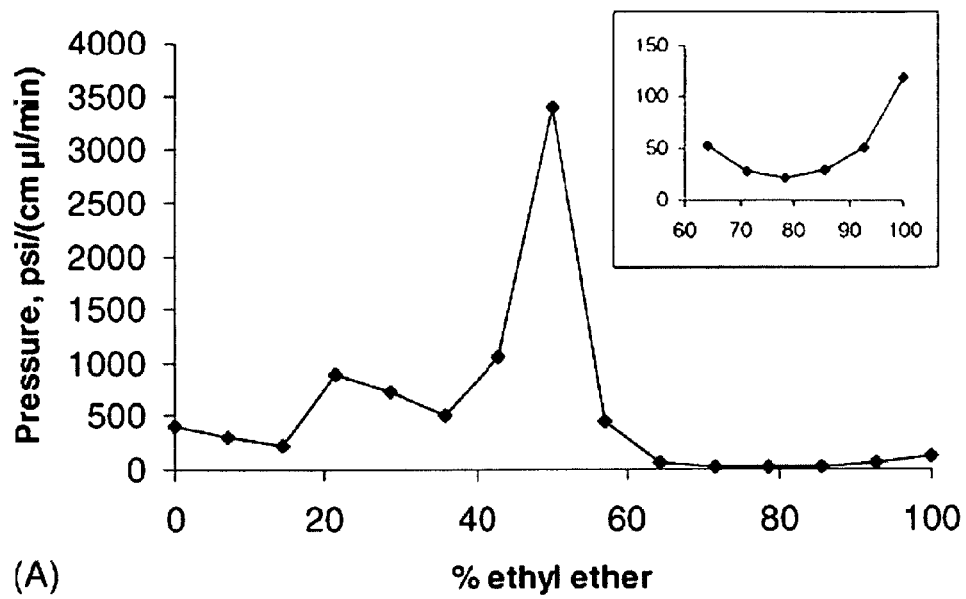
FIG. 2 shows a graph of flow resistance of the PEGMEA/PEGDA monolith. (A) Pressure drop dependence of the monolith on the percent of ethyl ether. Inset is the magnification of the section for ethyl ether of 60~100%. (B) Linear pressure dependence of the optimized PEGMEA/PEGDA monolith on the flow rates of water, THF and methanol.
Figure 2:
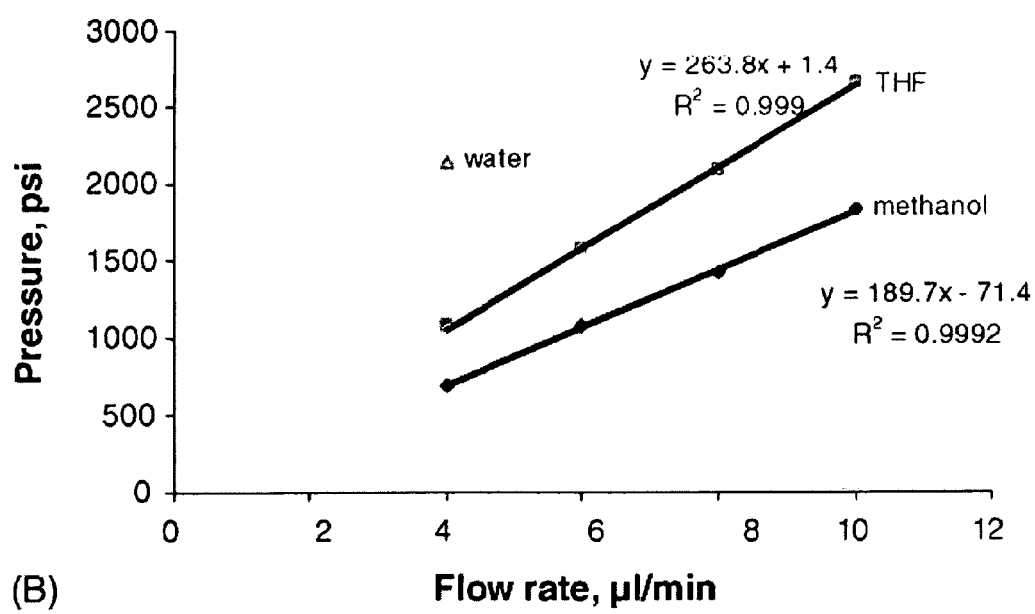

A quantitative index, the swelling propensity (SP), was defined by Nevejans and Verzele[26] to characterize the swelling and shrinking properties of a packed bed:

$$SP = \frac{p(\text{solvent}) - p(H_2O)}{p(H_2O)}$$

where p takes into account the viscosities of the solvent, and is defined as the ratio of pressure over solvent viscosity. By definition, SP=0 if no swelling or shrinking occurs, SP>0 if there is swelling, and SP<0 if the packed bed shrinks. From FIG. 2, the SP values for methanol and THF were calculated to be −0.44 and −0.08, respectively, assuming viscosities for water, methanol and THF of 1.025, 0.59 and 0.55 cP, respectively, at room temperature (data from the online CRC Handbook at 25° C.). This indicates that no significant shrinking or swelling of the PEGDA/PEGMEA monolith in THF was observed. Since THF can dissolve most hydrophobic polymers, the stability of the monolith in THF indicates that the monolith is relatively non-hydrophobic. However, shrinking of the monolith did occur in methanol, which unexpectedly had a positive effect because it improved the column permeability while maintaining a rigid structure. As shown in FIG. 2, when 2600 psi THF was applied to the monolithic column (4 cm×75 μm i.d.), no change in pressure drop was observed. This indicates high stability of the monolith, which is a result of the high concentration of crosslinker used in the monomer recipe.

Chromatographic Evaluation of the Monolith

Proteins were carefully selected to investigate the possibility of hydrophobic or ionic interaction with the monolithic material. Acidic (pepsin), basic (lysozyme) and hydrophobic (BSA) proteins were included. Several peptides with different molecular masses were also used to explore the elution mechanism of the monolithic column. Table D lists the molecular masses and pI values of the proteins and peptides used in this example.

Phosphate buffers (a) pH 7.0 with concentrations of 10, 20, 50, 100, 200, and 500 mM; (b) 10 mM concentration with pH values of 2.0, 4.0, 6.0, 8.0, 10.0, and 12.0; and (c) 100 mM concentration (pH 7.0) with additives of 0.5 M $Na_2SO_4$, 0.5 M NaCl, 10% ethylene glycol or 10% acetonitrile were used to elute the proteins. Buffers (a) and (c) were used to explore the possible hydrophobic interaction of the proteins with the monolith, and buffer (b) was used to investigate the possibility of any ionic interactions. In all cases, the proteins eluted earlier than thiourea. This indicates a SEC elution mechanism.

When buffer (a) was used, splitting of all of the protein peaks was observed when the buffer concentration was increased to 500 mM. However, the elution time was kept nearly constant for the proteins investigated within experimental error (except for the 500 mM buffer, because two retention times were obtained due to splitting of the peaks). For buffer (c), 0.5 M $Na_2SO_4$ in 100 mM (pH 7.0) also caused splitting of the protein peak This indicates possible hydrophobic interaction of the proteins with the monolith. However, 10% ethylene glycol or even 10% acetonitrile (α-chymotrypsinogen A formed a precipitate in the buffer with acetonitrile as an additive and, thus, could not be chromatographed) in buffer (c) provided elution of proteins in a similar way as 0.5 M NaCl additive. Not only were protein profiles similar to each other when buffer (c) was used, but the elution times were also close to each other. This strongly suggests that hydrophobic interaction, if any, would not be very significant.

The pH of buffer (b) was found to strongly affect the protein peak profiles. At pH 2.0, all proteins showed some degree of tailing, and α-chymotrypsinogen A and lysozyme exhibited peak splitting. Above pH 4.0, the symmetry of the protein peaks improved, except that lysozyme split into two peaks at all pH values. This indicates a possible ionic interaction between lysozyme and the monolith. However, as shown above, this weak ionic interaction disappeared when buffer (c) with 0.5 M NaCl additive (weak buffer ionic strength) was used.

In summary, good peak symmetries for all of the proteins were obtained with the use of buffer (c) with 0.5 M NaCl additive, i.e., 100 mM phosphate (pH 7.0) buffer containing 0.5 M NaCl, a condition often employed in high performance SEC of proteins. This indicates that the PEGMEA/PEGDA monolith had insignificant hydrophobic or ionic interactions with the proteins. It should be mentioned that all of the experiments described above employed high mobile phase flow rate (~1.10 mm/s) so that proteins eluted within ~3 min from a ~20 cm monolithic column. Such a flow rate facilitates the screening of buffers at the expense of skewing protein peaks. If a lower flow rate was used, improvement in peak symmetry could be achieved.

FIG. 5 (panel A) shows a chromatogram of a mixture of proteins and thiourea using low mobile phase flow rate. No separation between these proteins was observed. Injections of each protein under the same chromatographic conditions revealed that all five proteins with different molecular masses and pI values had almost the same elution time. In contrast, for the three peptides, a moderate separation was achieved, although they were not baseline resolved (see FIG. 5, panel B). A mixture of α-chymotrypsinogen A, the three peptides and thiourea was also injected into the column, and the chromatogram is shown in FIG. 5, panel C. Although the elution time for the protein was a little earlier than neurotensin (compare FIG. 5, panels A and B), coelution of α-chymotrypsinogen A and neurotensin was observed. Since we aimed to develop an inert, homogeneous monolith with pressure drop as low as possible, no further optimization of pore size distribution was attempted for SEC of proteins.

It should be mentioned that the peak shown in FIG. 5(A) was a coelution profile of five proteins and thus, it was relatively broad. Chromatography of each of the five proteins revealed a column efficiency of 6,000~8,000 plates/m and an asymmetric factor of 1.3~1.5 for a single protein. For peptides and thiourea, elution of each of them separately resulted in column plate counts of 9,000~20,000 plates/m and an asymmetric factor of <1.1. This roughly follows the trend of SEC, in which significantly lower plate counts for proteins than for small molecules have been observed due to the lower diffusion coefficients of the macromolecules. Typical plate counts in modem SEC (column dimensions of 250 mm×4.6 mm i.d.) ranged from 8,000 plates/m for proteins (i.e., amylase) to 34,000 plates/m for small molecules (i.e., glycyl tyrosine)[27]. For example, a plate count in SEC for α-chymotrypsinogen A was estimated to be ~5,600 plates/m based on a previously published chromatogram[28]. Thus, the plate counts achieved for proteins in this example with the use of the polymer monolith is acceptable. Furthermore, plate counts of 2,240~6,400 plates/m were reported for monolithic SEC of polystyrenes in THF[29].

ISEC Characterization of the PEGMEA/PEGDA Monolith

To further understand the separations of proteins and peptides shown in. FIG. 5, the porosity and pore size distribution of the PEGMEA/PEGDA monolith were investigated by ISEC. ISEC was originally used to characterize the structure of a packed bed with known probe compounds, e.g., polystyrene standards with narrow molecular mass distribution[30]. Guiochon and coworkers were among the first to use ISEC to characterize the porous structure of silica monoliths[31]. They defined several terms to describe the structure of a monolithic bed, such as total porosity, $\epsilon_t$, external porosity, $\epsilon_e$, and internal porosity, $\epsilon_i$. Based on ISEC, a pore size distribution of a monolith could also be derived assuming a simple correlation of $M_w = 2.25(10\,d)^{1.7}$, where $M_w$ is the molecular mass of the polystyrene standard and d is the diameter of the polystyrene standard in nm. Following the method of Gouichon et al.[31], we obtained an ISEC plot for the PEGMEA/PEGDA monolith, which is shown in FIG. 6, panel A The retention volumes, shown in FIG. 6 were the corrected retention volumes, taking into account the extracolumn volume of the chromatographic system, which was measured to be 248 nl, including the 60 nl internal sample loop. From FIG. 6 (panel A), the total porosity was calculated to be 75.4%, which is in agreement with the percent of porogen content in the monomer recipe (monolith 4 in Table C, 70% porogen used). The excluded molecular mass was estimated to be $10^4$, which corresponds to 14 nm. The external porosity was thus calculated to be 66.3% and the internal porosity was 9.1%. The relatively large total porosity (75.4%) accounts for the low flow resistance of the monolithic column.

The accumulated pore size distribution curve was derived from the ISEC calibration curve, and is shown in FIG. 6 (panel B). The pore volume fraction corresponding to pores larger than 304 nm was 77.8% (not drawn in the figure), and 7.0% for pores between 50 and 304 nm. The pore volume fraction for micropores (<2 nm) was 10.9%, and only 4.2% for mesopores (2 nm~50 nm). It can be seen that most of the pore volume fraction came from pores larger than 304 nm. The mesopore volume fraction was very small (4.2%), and the pore volume fraction in the range of 1.4~10.8 nm was only 1.1%. Since the stokes' radii for proteins in the molecular mass range of 10 K~70 K are between 1.5~3.6 nm (data from http://itsa.ucsf.edu/~hdeacon/Stokesradius.html), the monolith would predict no separation of the proteins used in this example. This explains the coelution of the proteins shown in FIG. 5 (panel A). In contrast, the pore volume fraction of micropores was relatively large (10.9%), and the curve (FIG. 6, panel B) in this pore size range was sharp. These two characteristics explain the separation of peptides (FIG. 5, panel B). Although the molecular mass difference between proteins and peptides was large, the difference between the pore volumes which excluded proteins and peptides was small, as can be seen in FIG. 6, panel B. This unique pore size distribution of the monolith explains why α-chymotrypsinogen A coeluted with neurotensin (FIG. 5, panel C).

In summary, the PEGMEA/PEGDA column shows SEC elution of peptides and proteins. The larger the molecule, the earlier the elution. However, due to the small pore volume fraction in the mesopores range of the monolith, separation between proteins could not be achieved using such monolithic columns.

Protein Recovery Evaluation

To further evaluate the protein adsorption properties of the PEGMEA/PEGDA monolith, a protein recovery experiment was performed. In conventional HPLC, the peak areas of a compound eluted from a packed column and stainless steel tubing were compared[28,32]. Because a strong dependence of peak area on mobile phase flow rate was observed in our capillary liquid chromatographic experiments, a direct comparison of the protein peak areas from monolithic and open tubular fused silica capillaries would not provide reliable data for calculating protein recovery. In contrast, the two detector method[33] or modified two detection window method[34,35] in capillary electrophoresis would be applicable for measuring protein recovery in the capillary format because peak areas are measured in one run and variations in detector or detection window responses are taken into account.

In our work, the two detection window method was used to perform recovery experiments. Thiourea was used as an internal standard to calibrate the detection window response variation. The recoveries for pepsin, BSA myoglobin, α-chymotrypsinogen A, and lysozyme were 98.0, 99.6, 103.5, 99.2, and 98.7%, respectively. This provides direct evidence that the PEGMEA/PEGDA monolith does not adsorb any significant amount of proteins under the conditions of 100 mM phosphate buffer (pH 7.0) containing 0.5 M NaCl.

Conclusions

A non-adsorptive monolith for proteins, PEGMEA/PEGDA, was prepared using methanol and ethyl ether as porogens. Complete conversion of the monomer to the polymer monolith could be finished in 10 min. The polymer monolith had very low flow resistance, and was macroscopically homogeneous. Protein recovery approached 100% if 100 mM phosphate pH 7.0 buffer containing 0.5 M NaCl was used as mobile phase. No significant ionic or hydrophobic interactions with proteins were found.

Another feature of this monolith is that it did not discriminate the elution of several proteins (molecular weight from 14 K to 67 K) studied. Together with the homogeneity and low flow resistance characteristics, the monolith would be very useful in situations requiring an inert material for protein analysis, such as in flow counteracting capillary electrophoresis[36,37] or electric field gradient focusing[21], in which the required hydrodynamic flow produces band broadening. By incorporating an inert material in the separation channel, sharpening of the protein bands is expected while maintaining the original separation/focusing mechanism. Currently, the incorporation of such a monolith into the separation/focusing channels of electric field gradient focusing devices[21] is under investigation. For SEC of proteins using this monolith, a reduction in through-pore diameter and optimization of the pore volume in the mesopore range must be accomplished. Unfortunately, this would be accomplished with a concomitant increase in flow resistance of the monolith.

TABLE C

Composition of reagent solution for various monoliths used [a,b]

| No. | DMPA | PEGMEA | EDMA | PEGDA | Ethyl ether | Other |
|---|---|---|---|---|---|---|
| 1 | 0.008 | 0.32 | 0.48 | — | — | 0.38 cyclohexanol + 0.58 dodecanol + 0.24 hexanes |
| 2 | 0.008 | — | 0.8 | — | 1.20 | — |
| 3 | 0.006 | — | — | 0.6 | 1.40 | — |
| 4 | 0.006 | 0.15 | — | 0.45 | 1.10 | 0.30 methanol |

[a] Units are in g.
[b] Recipes for monoliths 1 and 4 were optimized.

TABLE D

Proteins and peptides used.

| Analyte | Molecular mass | pI |
|---|---|---|
| bovine serum albumin[a] | 68,000 | 4.7 |
| pepsin[a] | 34,000 | <1 |
| α-chymotrypsinogen A[a] | 24,000 | 8.8 |
| Myoglobin[a] | 17,500 | 7.1 |
| Lysozyme[a] | 14,000 | 11.0 |
| Neurotensin[b] | 1,672.9 | 9.5 |
| angiotensin II fragment 3-8[b] | 774.9 | 7.8 |
| leucine enkephalin[b] | 555.6 | 5.9 |

[a] The molecular masses and isoelectric point pI values of proteins were obtained from "D. E. Schmidt, Jr., R. W. Giese, D. Conron, B. L. Karger, Anal. Chem. 52 (1980) 177."
[b] The molecular masses of peptides were read from the labels of the chemicals provided by Sigma-Aldrich, and the pI values were obtained from the EMBL Heidelberg European Molecular Biology Laboratory Program http://www.embl-heidelberg.de/cgi/pi-wrapper.pl).

Example II

This example illustrates manufacture and use of a monolith with strong cation exchange sites. The preparation of a stable polymer monolith by direct copolymerization of a high amount (40%) of 2-acrylamido-2-methyl-1-propanesulfonic acid and polyethylene glycol diacrylate was demonstrated for SCX liquid chromatography of peptides. The new polymer monolith was shown to improve peak capacity of ion exchange chromatography in which ion exchange of peptides is often considered relatively slow and less efficient than reversed-phase liquid chromatography for proteomics studies.[38]

SUMMARY

A stable poly(2-acrylamido-2-methyl-1-propanesulfonic acid-co-polyethylene glycol diacrylate) monolith was synthesized inside a 75 μm i.d. capillary by photoinitiated copolymerization with water, methanol and ethyl ether as porogens. The resulting monolith was evaluated for strong cation-exchange capillary liquid chromatography of both synthetic and natural peptides. Although the monolith possessed relatively strong hydrophobicity due to the use of 2-acrylamido-2-methyl-1-propanesulfonic acid as one monomer, the monolith had a high dynamic binding capacity of 157 μequiv peptide/mL, or 332 mg cytochrome c/mL. Exceptionally high resolution resulting from extremely narrow peaks was obtained, resulting in a peak capacity of 179 when using a shallow salt elution gradient. Although a second, naturally formed gradient might contribute to the sharp peaks obtained, high efficiency was mainly due to the use of polyethylene glycol diacrylate as a biocompatible crosslinker.

Experimental

Chemicals and Reagents. 2,2-Dimethoxy-2-phenyl-acetophenone (DMPA, 99%), 34-trimethoxysilyl)propyl methacrylate (98%), 2-acrylamido-2-methyl-1-propanesulfonic acid (AMPS), poly(ethylene glycol) diacrylate (PEGDA, Mn ~258), ethylene glycol dimethacrylate (EDMA) were purchased from Sigma-Aldrich (Milwaukee, Wis.) and used without further purification. Synthetic peptide standard CES-P0050 was obtained from Alberta Peptides Institute (Edmonton, Alberta, Canada). Bradykinin fragment 1-7, peptide standard P2693 and its nine components were from Sigma-Aldrich. Protein standards (myoglobin from equine skeletal muscle, cytochrome c from bovine heart, and lysozyme from chicken egg white) were also obtained from Sigma-Aldrich. Porogenic solvents for monolith synthesis and chemicals for mobile phase buffer preparation were HPLC or analytical reagent grade.

For digestion of beta-casein (Sigma-Aldrich), 1 mL of beta-casein digestion solution, which contained 50 μL of 1 M Tris pH 8.0 (99.9% purity, Fisher Scientific, Fair Lawn, N.J.), 10 μL of 0.1 M $CaCl_2$ (EM Science, Chemy Hill, N.J.), 20 μL of sequencing grade modified trypsin (Promega, Madison, Wis.), 100 μL of 2 mg/mL beta-asein, and 820 μL of Mili Q water, was incubated at 37° C. in a Shake' N' Bake hybridization oven (Boekel Scientific, Feasterville, Pa.) overnight. The digest was quenched by acidifying with formic acid. The beta-casein digest was then desalted using a Strata-X 33 μm polymeric sorbent column (Phenomenex, Torrance, Calif.), following the manufacturer's protocol. The eluent from the desalting column was lyophilized in a Centrivap cold trap (LabConco, Kansas City, Mo.), re-suspended in 20 μL of gradient elution starting buffer, and centrifugated using an Eppendorf centrifuge (Brinkmann, Westbury, N.Y.) at 10,000 rpm for 3 min before injection.

Polymer Monolith Preparation. Before filling the UV transparent capillary (75 μm i.d., 360 μm o.d., Polymicro Technologies, Phoenix, Ariz.) with monomer solution, the capillary inner surface was treated with 3-(trimethoxysilyl) propyl methacrylate to ensure covalent bonding of the monolith to the capillary wall.[20] The bulk monomer solution was prepared in a 1 dram (4 mL) glass vial by mixing 0.008 g DMPA, 0.32 g AMPS, 0.48 g PEGDA, 0.20 g water, 0.55 g methanol and 1.70 g ethyl ether. The monomer mixture was vortexed and ultrasonicated for 5 min to help dissolve AMPS and eliminate oxygen. Because of its low viscosity, the monomer solution was introduced into the UV transparent capillary by capillary surface action. The capillary (22 cm total length and 16.5 cm monomer length, unless otherwise specified) was then placed perpendicular to a UV dichroic mirror from Navitar (Newport Beach, Calif.), which was operated 45° directly under a Dymax 5000AS UV curing lamp (Torrington, Conn.) for 3 min. The resulting polymer monolith inside the capillary was connected to an HPLC pump, and flushed with methanol and water sequentially to remove porogens and any unreacted monomers. The prepared polymer monolith was then equilibrated with buffer solution before use. Care was taken to avoid drying the monolith by storing it filled with water or mobile phase. After the completion of all chromatographic experiments, a small section (2 cm) of the monolith inside the capillary was dried under vacuum for scanning electron micrography (SEM) analysis (FEI Philips XL30 ESEM FEG, Hillsboro, Oreg.).[39] The same procedure was also applied to synthesize poly(AMPS-co-EDMA) monoliths.

Capillary Liquid Chromatography (CLC). CLC of peptides was performed using a system previously described, with some modifications.[39] Briefly, two ISCO Model 100 DM syringe pumps with a flow controller (Lincoln, Nebr.) were used to generate a two-component mobile phase gradient. Due to the nL/min flow required for the monolithic capillary, the gradient flow from the pump was split with the use of a Valco splitting tee (Houston, Tex.), which was installed between the static mixer of the syringe pumps and the 60 nL Valco internal loop sample injector. A 33 cm long capillary (30 μm i.d.) was used as the splitting capillary, and a 5 cm long capillary (30 μm i.d.) was connected between the splitting tee and the injector to minimize extracolumn dead volume. The mobile phase flow rate was set at 69 μL/min. The actual flow rate in the monolithic capillary column was measured by monitoring movement of a liquid meniscus through 100 cm long open tubular capillary (75 μm i.d.), which was connected to the monolithic capillary using a Teflon sleeve (Hamilton, Reno, Nev.). Depending on the mobile phase used, the flow rate in the monolithic capillary was 70-100 nL/min, resulting in split ratios from 700:1 to 1000:1.

For CLC of peptides with gradient elution, mobile phase A was a 5 mM phosphate buffer (pH 2.7 or 7.0) with various amounts of acetonitrile. Mobile phase B was the same composition as mobile phase A plus 0.5 M NaCl, and a gradient rate of 1-5% B/min was typically used. All mobile phases were filtered through a 0.2 μm Nylon membrane filter (Supelco, Bellefonte, Pa.) and ultrasonicated before use. The apparent pH of the mobile phase was measured using a pH meter (Omego, Stamford, Conn.). On-column UV detection was performed at 214 nm. Chromatograms were transferred to an ASCII file and redrawn using Microcal Origin (Northampton, Mass.). The monolithic column was also used for CLC of proteins using aqueous buffers.

For measurement of the dynamic binding capacity of the monolithic column, 1 mg/mL bradykinin fragment 1-7 in 5 mM phosphate containing 40% acetonitrile (pH 2.7) was pumped under constant pressure of 2000 psi through the monolithic column (18.6 cm long, 75 μm i.d.) using one syringe pump. No splitter was used for these measurements. Because of the low amount (<1 mL) of the bradykinin fragment 1-7 solution available, it was preloaded into a sample loop capillary (2 m long, 320 μm i.d.), with one end connected to the Valco injector and the other end to the monolithic column using Upchurch unions (Oak Harbor, Wash.). The flow rate was measured to be 91 nL/min. Following the same procedures, the dynamic binding capacity based on uptake of protein (cytochrome c) was also performed on a new monolithic column (7 cm long, 75 μm i.d.). A solution of 4 mg/mL cytochrome c in 5 mM phosphate (pH 6.2) was pumped through the column under constant pressure of 850 psi, resulting in a column flow rate of 91 nL/min.

For studying the swelling/shrinking properties of the polymer monolith, different organic solvents were pumped through a 10 cm long monolith segment inside a capillary at different pressures. A splitter and detector were not used for these measurements. The flow rate was measured as described above.

Results and Discussion

Polymer Monolith Preparation. AMPS, a commercially available acrylamido derivative, was chosen as monomer to synthesize the SCX monolithic column because it contains the desirable sulfonate group. PEGDA, which is an acrylate based crosslinker with three ethylene glycol units, has been shown to resist adsorption of peptides and proteins.[39] Therefore, it was selected as crosslinker for the synthesis of the monolith. PEGDA was used instead of EDMA as crosslinker to prepare a monolith with more hydrophilicity.

The most widely used porogen strategy was adopted to control the throughpores in the monoliths. To date, choice of porogens has been mainly achieved by trial-and-error, although some theoretical aspects for porogen selection have been derived for macroporous particle synthesis using suspension polymerization.[40-42] Because the solubility of AMPS in common organic solvents is low, water was selected as one of the porogens to help dissolve AMPS. Methanol was selected as another porogen because it was proven efficient for the formation of macroporous throughpores in a poly (PEGDA) monolith.[39] Unfortunately, any combination of water and methanol (with 0.32 g AMPS and 0.48 g PEGDA) yielded a nonporous or microporous translucent gel structure which allowed no flow of mobile phase. The same results were also observed for combination of water, methanol and 1-propanol. Since ethyl ether is another powerful porogen for PEG-based monoliths,[39] it was finally chosen as the third porogen. After simple optimization, a recipe (25% monomers, composed of 40:60 wt % AMPS and PEGDA, and 75% porogens, composed of 8:23:69 wt % water, methanol and ethyl ether) was finalized, and the resulting monolith supported considerable flow under moderate pressure in aqueous buffer. Noteworthy was the incorporation of 40% AMPS, which represents the highest reported percentage of AMPS copolymerized into a polymer monolith backbone. Due to the one-step in-situ synthesis protocol, the rate of success in preparing such monolithic capillary columns approached 100%.

A scanning electron micrograph of the optimized monolith is shown in FIGS. 7(A) and 7(B). It can be immediately observed that the morphology of the poly(AMPS-co-PEGDA) monolith is quite unique. It was composed of fused microglobules, with no distinct microspheres. It appeared intermediate between a conventional polymer monolith with a distinct particulate structure[43-45] and a silica monolith with a skeletal structure.[16-17] The throughpores of the monolith were obvious. Cracks along the circumference of the monolith (FIG. 7(A)) were presumably due to shrinking of the monolith upon drying when SEM images were taken.

To explore variables that could result in the formation of this unique morphology, two other monoliths were prepared and their SEM photographs are shown in FIGS. 7(C) and 7(D). With an increase in methanol in the porogen composition, conventional polymer monolithic morphology with discrete and more "regular" microglobules was formed (FIG. 7(C)). If EDMA was used as crosslinker, the resulting poly (AMPS-co-EDMA) monolith exhibited similar fused but more porous structure (compare FIGS. 7(B) and 7(D)). Based on these micrographs, it seems that porogens rich in methanol or the use of EDMA as crosslinker favored the formation of conventional polymer monolithic morphology, while a monolith formed from porogens rich in ethyl ether, or that used PEGDA as crosslinker tended to form a fused structure. Both porogen and crosslinker are factors that control the morphology of poly(AMPS) monoliths.

Effect of Acetonitrile on the Elution of Synthetic Peptides. An ideal SCX column for LC of peptides should be moderately hydrophilic, able to retain weakly charged analytes (e.g., +1 charged peptides), and exhibit retention of analytes independent of buffer pH from acidic to neutral.[46] In addition, high binding capacity is another favorable feature which improves peptide resolution.

Hodges et al.[46,47] designed several synthetic peptides to evaluate particle based SCX columns. The synthetic peptide standard, CES-P0050, was composed of four peptides (see Table E) which possess certain characteristics for SCX column evaluation. These peptides are all undecapeptides having similar chain length to those most commonly encountered in protein tryptic digests, and they do not have any acidic residues (the C-terminal groups are amides), so they possess the same charge in acidic to neutral buffers. The hydrophobicity index of these peptide standards has been compiled for pH 7.0.[47] However, they were re-tabulated in Table E for easy reference, along with other properties (e.g., amino acid sequence).

FIG. 8 shows a gradient elution chromatogram of the synthetic peptides under different buffer conditions using the poly(AMPS-co-PEGDA) monolithic SCX column. With an increase in acetonitrile in the mobile phase from 0% to 40% (see FIG. 8(A) to 8(E)), the elution times for peptides 1-4 were monotonically decreased. For peptide 4, addition of 40% acetonitrile in the elution buffer was required to suppress hydrophobic interactions (compare FIG. 8(D) and FIG. 8(E)). For the less hydrophobic peptides 2 and 3, 20-30% acetonitrile could effectively eliminate hydrophobic interactions, as evidenced by the very sharp peaks obtained. For the least hydrophobic peptide 1, no acetonitrile was required because no significant hydrophobic interactions were observed. The minor differences in retention times for peptide 1 were likely due to differences in mobile phase column flow rate. The dramatic decrease in retention time and improvement in peak shape for peptide 4 indicates relatively strong hydrophobicity of the poly(AMPS-co-PEGDA) monolith. This feature is not desirable for two-dimensional LC (e.g., ion exchange followed by reversed-phase) for proteomics, in which an aqueous buffer without acetonitrile is required in the first dimension to effect retention of peptides in the second dimension before separation.

The relatively strong hydrophobicity of the poly(AMPS-co-PEGDA) monolith was surprising. The biocompatible crosslinker PEGDA was specially designed and used to decrease unwanted polymer backbone hydrophobicity. To further confirm the biocompatibility of PEGDA, a poly (PEGDA) monolith was prepared following a previously published protocol,[39] and peptides 1-4 were eluted from the monolith using buffers containing various amounts (0-40%) of acetonitrile. Results (data not shown) indicated negligible differences in peptide elution with the use of different buffers. Therefore, the relatively strong hydrophobicity of the poly(AMPS-co-PEGDA) monolith must be due to the monomer AMPS itself. In fact, the AMPS molecule contains an isobutyl arm, which connects to the sulfonate group on one end and the acrylamido group on the other end. Alpert et al.[48] found that PolySulfoethyl A columns were superior to the more hydrophobic sulfopropyl columns.[49,50] In analogy, it is expected that the monolithic sulfobutyl phase possesses stronger hydrophobicity than desired due to the butyl segment in the side groups.

Despite the strong hydrophobicity of the poly(AMPS-co-PEGDA) monolith, it was shown to retain strongly the +1 charged peptide (see FIG. 8(E)). This positive feature is uncommon for commercially available particulate SCX columns where only the PolySulfoethyl A column could retain the peptide.[46,47] For 40% acetonitrile, where any hydrophobic interaction was greatly eliminated, retention of the peptide on the monolith would be expected from ionic interaction only. This strong ionic interaction can be attributed to the use of a high amount of AMPS (40%) in the copolymerization.

With hydrophobic interactions suppressed (i.e., with the use of 40% acetonitrile), the four synthetic peptides were eluted as extremely sharp peaks (see FIG. 8(E)), with an average peak width at baseline of 0.28 min. According to the simple definition of peak capacity in gradient elution (peak capacity=time of gradient/peak width),[51] the peak capacity was calculated to be 71, a value surpassing most particulate based SCX columns[46,48-50,52-56] (Peak capacities of 24~66 were estimated based on several chromatograms provided in these references) and other polymer monolithic SCX columns[15,57-60] (Peak capacities of 5~32 were again estimated; in cases of isocratic elution, the peak capacity was calculated as $n=(\sqrt{N}/4)\ln(t_2/t_1)$, where N is the column efficiency, and $t_2$ and $t_1$ are the retention times of the last and the first eluting peaks, respectively]. The asymmetry factors calculated at 10% peak height for peptides 1-4 were 1.01, 0.94, 0.90, and 0.99, respectively. The sharp peaks together with minimal fronting or tailing indicated a highly efficient SCX monolithic column.

The run-to-run reproducibility of the poly(AMPS-co-PEGDA) column was good. For three consecutive runs using conditions the same as in FIG. 8(E), the relative standard deviation (RSD) of the retention times for peptides 1-4 were 1.9, 0.7, 0.3, and 0.4%, respectively. For peak height, the RSD values for peptides 1-4 were 4.6, 2.3, 2.0 and 1.7%, respectively. These data clearly demonstrate that good reproducibility could be readily achieved if the column was equilibrated with starting buffer for a sufficient period (typically ~10 column volumes) between runs, although the polymer monolith exhibited swelling in aqueous buffers (vide infra).

Column-to-column reproducibility measurements gave retention time RSD values (n=3) for peptides 1-4 of 1.3, 1.6, 2.2, and 2.4%, respectively. However, significant deviation was observed for peak height measurements; the RSD values for peptides 1-4 were 18.5, 18.6, 34.6, and 21.9%, respectively.

Effect of Buffer pH on the Resolution of Synthetic Peptides. With an increase in buffer pH from 2.7 to 7.0, greater retention with similar sharp peaks was observed for synthetic peptides 1-4 under otherwise identical conditions as in FIG. 8(E) (data not shown). Because the peptides bear the same charges in both buffer pHs (see Table E), this indicates an increased negative charge density of the monolith upon an increase in buffer pH. Although AMPS is a strong organic acid with pKa of 1.2,[61] the pKa of poly(AMPS) shifts to a higher value due to the absence of electron-withdrawing vinyl groups upon polymerization.[62] An increase in metal-poly(AMPS) retention was observed with an increase in buffer pH from 1 to 7.[63] Thus, the lower acidity of poly(AMPS) over AMPS accounts primarily for the increased retention of peptides at pH 7.0 compared to pH 2.7. Another contributing factor is the presence of acrylic acid, an impurity found in both AMPS and PEGDA monomers, which can be copolymerized into the monolith backbone. However, no confirmation of this was sought. The stronger retention of peptides upon increase of buffer pH was also observed for most particulate based SCX columns.[46]

Dynamic Binding Capacity. An important property of an ion exchange column is the binding capacity,[64] which determines the resolution, column loadability, and gradient elution strength. For the measurement of dynamic binding capacity of an SCX column, proteins (e.g., lysozyme or hemoglobin) are often used. Although the monolithic column could elute and separate proteins using buffers with high ionic strength (vide infra), it did not elute lysozyme, cytochrome c or hemoglobin within 2 h under conditions typical for SCX chromatography of peptides [e.g., 5 mM phosphate (pH 2.7) containing 40% acetonitrile and 0.5 M NaCl]. Therefore, bradykinin fragment 1-7, which bears +2 charge at pH 2.7, was used to determine the monolithic column dynamic binding capacity. During frontal analysis, a sharp increase in baseline was observed, indicating fast kinetic interaction of the peptide with the column. With the use of 1 mg/mL peptide, it took an amazingly long time (1074 min) to saturate the column. Based on the measured flow rate of 91 nL/min, the dynamic binding capacity was 119 mg/mL, corresponding to 157 µequiv/mL. From the monolith recipe (see Experimental Section), this 40% AMPS/60% PEGDA monolith had a theoretic binding capacity of 475 µequiv/mL. This indicates that ~33% of AMPS in the monolith backbone was accessible for ionic interaction. The major portion (67% in this case) of AMPS is most likely buried in the polymer monolith, due to the direct copolymerization method used. Nevertheless, the dynamic binding capacity of the poly(AMPS-co-PEGDA) monolith was high. This was supported by the elution of the +4 charged peptide 4 as shown in FIG. 8(E) after a 20 min gradient step. For simple comparison with other SCX columns, the dynamic binding capacity was also measured based on cytochrome c uptake although such measurement might be inappropriate and inaccurate due to hydrophobic binding. It took 282 min to saturate the 7 cm long monolith, resulting in a binding capacity of 332 mg/mL.

The dynamic binding capacity of our monolith was compared with other columns. Alpert et al.[48], reported that the PolySulfoethyl A column had a dynamic binding capacity of 100 mg hemoglobin/mL packing material, corresponding to ~3 µequiv/mL. Because 157 µequiv peptide/mL or 332 mg protein/mL was achieved for the current monolithic column, the binding capacity was greater than that of the PolySulfoethyl A column. For the poly(glycidyl methacrylate-co-ethylene glycol dimethacrylate) monoliths[57,65] grafted with AMPS for SCX chromatography of proteins, the dynamic binding capacity was found to be typically lower than 100 mg protein/g monolith. For the functionalized poly(glycidyl methacrylate-co-ethylene glycol dimethacrylate) monolith,[58] the dynamic binding capacity was 90-300 µequiv/mL, albeit based on copper ion uptake. The binding capacity was very low (~1 µequiv/mL) for the anion exchange polymer monolith,[59] which was prepared by agglomeration of aminated latex particles to a monolith prepared through the copolymerization of a small amount of AMPS, a large amount of butyl methacrylate and EDMA. This was presumably due to the lower amount of AMPS used in the copolymerization. In summary, the dynamic binding capacity of the current monolith, which was prepared from direct copolymerization of 40% AMPS and 60% PEGDA, was greater than the particulate-based SCX PolySulfoethyl A column and most of the other polymer monolithic SCX columns.

SCX Chromatography of a Complex Peptide Mixture. To demonstrate the general utility of the poly(AMPS-co-PEGDA) monolith for peptide analysis, a more complex peptide mixture P2693 composed of 9 natural peptides (see Table F) was chromatographed using buffer containing 40% acetonitrile under different gradient rates (FIG. 9). As seen in FIG. 9 (A), 7 out of the 9 peptides were resolved when 5% B/min gradient rate was used. By decreasing the gradient rate to 2% B/min, 8 peaks were baseline separated (FIG. 9 (B)). A further decrease in the gradient rate to 1% B/min resolved all 9 peptides, although peptides 2 and 3 were not baseline separated (FIG. 9 (C)). Thus, it is convenient to use a shallow gradient to improve resolution for analyzing complex samples. The separation shown in FIG. 9 (C) was governed by an ion exchange mechanism. Following the empirical relationship between retention time and charge-to-chain length ratio developed by Hodges et al,[46] a straight line [$t_R$=66.03× N/ln(n)−2.05] was obtained with a regression coefficient of 0.96, where $t_R$ is the peptide retention time, N is the charge, and n is the number of amino acid residues. This confirmed a pure ionic interaction of the polymer monolith for SCX of natural peptides with 5 to 14 residues and a hydrophobicity range from 7.5 to 34.9 (see Table F).

It is interesting that the elution order in FIG. 9 (C) is the reverse of that in capillary zone electrophoresis (CE) (cf technical bulletin for P2693 from Sigma, http://www.sigmaaldrich.com/sigma/datasheet/p2693dat.pdf) except for peptides 7 and 8. This is not unexpected because retention in SCX is based on the charge-to-ln(chain length) ratio while in CE, migration is determined by analyte charge-to-size ratio. Thus, an analyte with more charge and smaller size will migrate earlier in CE, and elute later in SCX. As compared with separation in CE, better resolution (with the exception of peptides 2 and 3) were generally obtained for SCX chromatography, although longer time was required. Peak widths were somewhat narrower in SCX chromatography than in CE. This demonstrates that comparable or better resolution and efficiency was achieved for peptide analysis with the use of the poly(AMPS-co-PEGDA) monolithic column than for CE.

The average peak width at baseline in FIG. 9(A) (excluding the second peak due to coelution of three peptides), FIG. 9(B) (excluding the second peak due to coelution of two peptides) and FIG. 9(C) (excluding the second and third peaks due to incomplete resolution) were 0.27, 0.38 and 0.56 min, resulting in peak capacities of 74, 130 and 179 for the gradient rates of 5%, 2% and 1% B/min, respectively. As discussed above, the peak capacity calculated from FIG. 8 (E) was 71 where a gradient rate of 5% B/m in was used for SCX of four synthetic peptides. It seems that the peak capacity depends on the salt gradient rate and not on the analytes used. A shallower gradient resulted in a greater peak capacity. This was due to the use of the unique monolith, for which the peak width increased less proportionally upon an increase in the gradient elution time. This feature is attractive for resolving complex peptide samples (e.g., protein digests).

Noteworthy was the resolution between methionine enkephalin and leucine enkephalin (inset in FIG. 9 (C)). These two peptides bear the same charge and have the same chain length (see Table F). They also have very similar molecular weight and hydrophobicity. Due to the use of 40% acetonitrile in the mobile phase, it is not likely that the resolution was based on differences in hydrophobicity. Instead, the separation was primarily due to differences in ionic interaction resulting from a minor difference in molecular weight. Because methionine enkephalin has a greater molecular weight than leucine enkephalin, the ionic interaction between methionine enkephalin and the monolith would be expected to be somewhat smaller, leading to earlier elution. The successful separation of methionine enkephalin and leucine enkephalin emphasizes the exceptional resolution provided by the poly(AMPS-co-PEGDA) monolith.

Further evaluation of the monolith was conducted for SCX chromatography of a beta-casein digest (FIG. 10). Once again, very nice separation was obtained. Based on several completely resolved peaks (indicated on FIG. 10), the peak capacity was estimated to be 167, close to 179 measured using peptide standard P2693. This confirmed that peak capacity was not dependant on the sample analyzed, but on the gradient rate. It should be mentioned that the protein digest had to be desalted. If the beta-casein digest was not desalted (see Experimental Section), the peptides coeluted in 15 min (data not shown). This is expected because peptides will not be strongly retained if they are dissolved in a high concentration of salt buffer. During the experiment, it was also important to use freshly prepared peptides and to store them in a refrigerator. For example, peptide standard CES-P0050 degraded if dissolved in the starting buffer and stored at 2-8° C. for more than 2 months. FIG. 11 shows a separation of a degraded sample. In addition to the main four peptides, eight other peptides could be clearly seen. This, once again, demonstrates the high resolution of the poly(AMPS-co-PEGDA) monolith for SCX liquid chromatography of peptides. It opens the possibility of using SCX chromatography for quality analysis (e.g., purity) of peptides, although such analyses are almost exclusively performed using reversed-phase liquid chromatography.

SCX Chromatography of Protein Standards. Attempt was also made to perform SCX chromatography of basic proteins, and the result is shown in FIG. 12. As mentioned before, proteins did not elute from the monolithic column when 5 mM phosphate (pH 2.7) containing 40% acetonitrile and 0.5 M NaCl was used as eluent. This is likely due to stronger binding of proteins than peptides, as confirmed by the elution of proteins when NaCl concentration was increased to 2.0 M. However, due to the poor solubility of NaCl in 40% acetonitrile, a buffer that contains no acetonitrile must be used. Thus, the separation in FIG. 12 was based on a mixed-mode mechanism. An increase in buffer salt concentration resulted in a decrease in ionic interaction and an increase in hydrophobic interaction. As a result, proteins peaks were broadened by the increased nonspecific hydrophobic interaction during salt gradient elution. Although the SCX column exhibited worse chromatographic performance for proteins than for peptides, it was comparable to other monolithic SCX columns for protein analysis.[57]

Stability of the Poly(AMPS-co-PEGDA) Monolith. Permeability is a good index to reflect swelling or shrinking of the monolith. If a monolith swells, its throughpores will decrease in size, resulting in lower permeability, and vise versa. From Table G, the permeability was approximately an order of magnitude lower in aqueous buffer than in some organic solvents. With the use of organic solvents, the permeability decreased roughly with an increase in solvent relative polarity, except that ethyl ether and acetone had the highest permeability. This indicates that the monolith swells in more polar solvents and shrinks in less polar solvents.

Although the poly(AMPS-co-PEGDA) monolith swelled in aqueous buffer and shrank in organic solvents, no detachment of the monolith from the capillary wall was observed under any condition, likely due to covalent attachment to the capillary wall. Furthermore, the column flow rate reached a constant value after equilibration with a new solvent. This indicated reversible shrinking or swelling of the monolith under a variety of solvent conditions. For the SCX liquid chromatography of peptides in the example, the column flow rate measured was 70-100 nL/min when the backpressure read from the pump panel was between 2000 and 2300 psi during the gradient run. This indicates that a considerable flow was generated at moderate pressure even though the monolith swelled. The polymer monolith could be used continuously over 1 month under a pressure of >2000 psi. Excessive swelling of the sulfonate-containing polymer monolith in aqueous buffer, which would result in no flow, was not observed for the poly(AMPS-co-PEGDA) monolith reported in this example.

Tentative Explanation of the Sharp Peaks Obtained. It is interesting that the permeabilities of the monolith in aqueous buffers A and B were different (see Table G). An increase in permeability was observed with the use of the same buffer with 0.5 M NaCl additive. This reflects a responsive property of the poly(AMPS-co-PEGDA) monolith upon contact with salt. Viklund et al.[65] reported that poly(trimethylolpropane trimethacrylate) monolith [poly(TRIM)] with a surface grafted with N,N-dimethyl-N-methacryloxyethyl-N-(3-sulfopropyl) ammonium betaine (SPE) showed a salt dependant permeability. However, the permeability decreased with an increase in NaCl concentration in the range of 0-0.2 M. Interestingly, no such trend was observed for the monolith prepared by copolymerization of TRIM and SPE.

The salt dependant permeability of the poly(AMPS-co-PEGDA) monolith is expected to have an influence on the chromatography of peptides. The mobile phase flow rate in the monolithic column increased in our system during the salt gradient run because the nano flow gradient in the column was generated by a passive splitter (see Experimental Section). Thus, two gradients effected the elution of peptides from the monolithic column. One was a simple salt gradient, which narrowed the peptide bands during elution. The other was a naturally formed flow gradient. The flow gradient would provide an effectively sharper salt gradient than set in the program. As seen in FIG. 9, the sharper the salt gradient, the narrower the peak widths. Double gradient elution was previously demonstrated in ion exchange liquid chromatography of small ions, where a flow gradient was intentionally employed to achieve fast separation.[66] It should be emphasized that although a natural flow rate gradient existed in these studies, it did not contribute significantly to the sharpening of peptide bands, especially under shallow (e.g., 1% B/min) salt gradient conditions, where a flow rate increase of ~1.4 times (based on Table G) was estimated for a 100 min interval.

It is hypothesized that the extremely sharp peaks achieved in this example are primarily due to the nature of the poly (AMPS-co-PEGDA) monolith. While the poly (AMPS-co-PEGDA) monolith was shown to exhibit strong hydrophobicity, the hydrophobicity was mainly derived from the side chains of the monolith that attached the functional AMPS monomer. The backbone of the polymer monolith contributed negligible hydrophobicity due to the use of both a biocompatible crosslinker PEGDA and a biocompatible acrylamido group in the AMPS. Thus, no nonspecific hydrophobic interaction between the polymer backbone and peptide would occur. Because the side chains are located on the surface of the polymer monolith upon contact with aqueous buffer, mass transfer resistance would be small, resulting in high column efficiency. To test this hypothesis, SCX chromatography of synthetic peptides 1-4 on a poly(AMPS-co-EDMA) monolith was performed under the same conditions as in FIG. 8(E). Although well separated, the peaks for all four peptides were broad and tailing (data not shown). This observation confirms that the extremely narrow peaks obtained in this example were primarily due to the use of the biocompatible crosslinker PEGDA.

CONCLUSIONS

A poly(AMPS-co-PEGDA) monolith containing as high as 40% AMPS was prepared by one-step copolymerization. The monolith had several favorable features, such as high binding capacity, extraordinary high resolution and high peak capacity, making it ideal for resolving complex peptide samples, such as protein digests. Due to its excellent chromatographic performance and ease of preparation, the poly(AMPS-co-PEGDA) monolith is expected to find many applications.

A unique structural feature of the new monolith is the use of PEGDA instead of the conventional EDMA crosslinker, which is believed to result in the high resolution and sharp peaks obtained for peptide analysis. Due to the hydrophobicity of the AMPS monomer, a better monolith could be obtained if a more hydrophilic functional monomer was used. For example, if acrylamido methanesulfonic acid or 2-acrylamido-1-ethanesulfonic acid was used in place of AMPS, the hydrophobicity of the resulting monolith would be dramatically decreased. This should, in turn, provide even better separation of peptides and make efficient SCX of proteins possible with aqueous buffers containing no acetonitrile. Unfortunately, neither of the two monomers is commercially available. We are currently investigating their synthesis.

Another possible alternative functional monomer is the commercially available vinyl sulfonic acid. Unfortunately, it may be challenging to design suitable porogens to copolymerize vinyl sulfonic acid and PEGDA because it is well known that the polymerization rate of vinyl and acrylamido groups is different. Another difficulty is the unavailability of pure vinyl sulfonic acid. For example, sodium vinylsulfonate, a sodium salt of vinyl sulfonic acid, is available through Sigma as ~30% solution in $H_2O$. This further complicates the porogen design because the ratio of vinyl sulfonic acid to water is fixed at 3 to 7 if 30% sodium vinylsulfonate is used.

TABLE E

Properties of Synthetic Peptides

| Analyte | Amino acid sequence[a] | Charge at pH 2.7 | Charge at pH 7.0 | Hydrophobicity index at pH 2.0[b] | Hydrophobicity index at pH 7.0[c] |
|---|---|---|---|---|---|
| 1 | Ac-Gly-Gly-Gly-Leu-Gly-Gly-Ala-Gly-Gly-Leu-Lys-amide | +1 | +1 | 14.7 | 18.6 |
| 2 | Ac-Lys-Tyr-Gly-Leu-Gly-Gly-Ala-Gly-Gly-Leu-Lys-amide | +2 | +2 | 17.5 | 23.4 |
| 3 | Ac-Gly-Gly-Ala-Leu-Lys-Ala-Leu-Lys-Gly-Leu-Lys-amide | +3 | +3 | 21.4 | 30.2 |
| 4 | Ac-Lys-Tyr-Ala-Leu-Lys-Ala-Leu-Lys-Gly-Leu-Lys-amide | +4 | +4 | 24.2 | 35.0 |

[a]Amino acid sequence was from ref [47]. Ac = N$_\alpha$-acetyl; Amide = C$_\alpha$-amide. Positively charged residues were indicated in bold font.
[b]Hydrophobicity index was calculated based on ref [67].
[c]Data were from ref [47].

TABLE F

Properties of the Nine Peptides in the P2693 Standard

| No | Analyte | Amino acid sequence[a] | Molecular weight | No. of residues | Charge at pH 2.7 | Hydrophobicity index at pH 2.0[b] |
|---|---|---|---|---|---|---|
| 1 | Oxytocin | Cys-Tyr-Ile-Gln-Asn-Cys-Pro-Leu-Gly-NH$_2$ | 1007.19 | 9 | +1 | 19.5 |
| 2 | Methionine enkephalin | Tyr-Gly-Gly-Phe-Met | 573.70 | 5 | +1 | 10.0 |
| 3 | Leucine enkephalin | Tyr-Gly-Gly-Phe-Leu | 555.62 | 5 | +1 | 12.6 |
| 4 | Bombesin | pGlu-Gln-Arg-Leu-Gly-Asn-Gln-Trp-Ala-Val-Gly-His-Leu-Met-NH$_2$ | 1619.85 | 14 | +2 | 34.9 |
| 5 | Luteinizing hormone releasing hormone | pGlu-His-Trp-Ser-Tyr-Gly-Leu-Arg-Pro-Gly | 1183.27 | 10 | +2 | 20.4 |
| 6 | [Arg8]-Vasopressin | Cys-Tyr-Phe-Gln-Asn-Cys-Pro-Arg-Gly-NH$_2$ | 1084.23 | 9 | +2 | 11.5 |
| 7 | Bradykinin fragment 1-5 | Arg-Pro-Pro-Gly-Phe | 572.66 | 5 | +2 | 7.5 |
| 8 | Substance P | Arg-Pro-Lys-Pro-Gln-Gln-Phe-Phe-Gly-Leu-Met-NH$_2$ | 1347.70 | 11 | +3 | 27.9 |
| 9 | Bradykinin | Arg-Pro-Pro-Gly-Phe-Ser-Pro-Phe-Arg | 1060.20 | 9 | +3 | 16.8 |

[a]Amino acid sequence was from Sigma website. Positively charged residues were indicated in bold font. Free N-terminal bears +1 charge while pyroed N-terminal with glu (pGlu) is neutral.
[b]Hydrophobicity index was calculated based on ref [67].

TABLE G

Permeability of the Poly(AMPS-co-PEGDA) Monolith

| Flushing fluid | Relative polarity[a] | Viscosity, $\eta$ (cP)[b] | Column back-pressure, $\Delta p$ (psi) | Linear velocity, u (mm/s) | Permeability, k ($\times 10^{-15}$ m$^2$)[c] |
|---|---|---|---|---|---|
| Hexane | 0.009 | 0.300 | 800 | 5.52 | 30.0 |
| Ethyl ether | 0.117 | 0.224 | 800 | 12.09 | 49.1 |
| THF | 0.207 | 0.456 | 800 | 2.51 | 20.8 |
| Acetone | 0.355 | 0.306 | 800 | 9.09 | 50.4 |
| Acetonitrile | 0.460 | 0.369 | 800 | 3.30 | 22.1 |
| Methanol | 0.762 | 0.544 | 800 | 1.17 | 11.5 |
| Water | 1.000 | 0.890 | 1200 | 0.27 | 2.9 |
| Buffer A | / | 0.846 | 1200 | 0.33 | 3.4 |
| Buffer B | / | 0.890 | 1200 | 0.47 | 5.1 |

[a]Relative polarity data were from http://virtual.yosemite.cc.ca.us/smurov/orgsoltab.htm.
[b]Viscosity data were from online CRC Handbook of Chemistry and Physics, 85th edition, 2004-2005. For buffer A which contains 40% acenonitrile, the viscosity is ~95% water (Sadek, P. C., in HPLC Solvent Guide, 2nd ed., John Wiley and Sons: New York, 2002). For buffer B which contains both 40% acetonitrile and 0.5 M NaCl, the viscosity is assumed to be 0.89 × 0.95 × 1.052 = 0.890 because 0.5 M NaCl is 1.052 times the viscosity of pure water.
[c]Permeability k = $\eta$ Lu/$\Delta$p, where $\eta$ is the viscosity, L is the column length (10 cm in this case), u is the solvent linear velocity, and $\Delta$p is the column backpressure.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A monolith for liquid chromatography comprising a continuous mesoporous skeletal structure with nanometer-sized pores in the skeletal structure, the skeletal structure essentially non-adsorptive to proteins with a functional group selected to impart a desired interaction property to the monolith, the skeletal structure providing structural integrity to the monolith, the skeletal structure comprising reaction product of;
crosslinker having at least three adjacent groups, selected from ethylene oxide, polyethylene oxide, and mixtures thereof, and two or more pendent vinyl groups,
monomer having the formula,

CH$_2$=CR—Y—Z where R is H or CH$_3$,
where Z is the functional group selected to impart a desired interaction property to the monolith, and
where Y is nothing, or any group that will not materially affect or compete with the function of the functional group (Z) in the monolith, or the reactivity of vinyl groups in the crosslinker or monomer.

2. A monolith for liquid chromatography as in claim 1 wherein the crosslinker comprises;

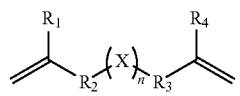

where n is equal to or greater than 3,
X is —CH$_2$CH$_2$O—, or —CH(CH$_3$)CH$_2$O—, or —CH$_2$CH$_2$CH$_2$O—, or a mixture thereof, R$_1$ and R$_4$ are the same or different and are —H, or —CH$_3$,
R$_2$ is selected from the group consisting of

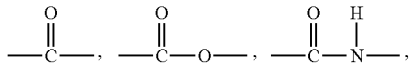

—O—, or is nothing, and
R$_3$ is selected from the group consisting of

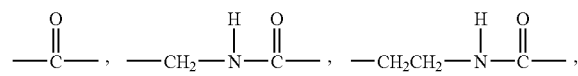

—CH$_2$CH$_2$—, or is nothing.

3. A monolith for liquid chromatography as in claim 1 wherein the crosslinker comprises one or more selected from the group consisting of;

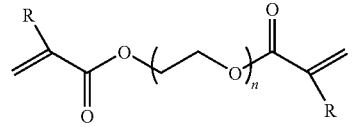

and

where R is CH$_3$ or H, and n is equal to or greater than 3.

4. A monolith for liquid chromatography as in claim 1 wherein Y is nothing, —CH$_2$—, —CO—, —NH—, —C(CH$_3$)$_2$—, —(CH$_2$CH$_2$O)$_n$—, —(CH(CH$_3$)CH$_2$O))$_n$—, or —O—.

5. A monolith for liquid chromatography as in claim 1 wherein Z is selected to form a monolith for ion exchange liquid chromatography, chiral liquid chromatography, reversed phase liquid chromatography, hydrophobic interaction liquid chromatography, or size exclusion liquid chromatography.

6. A monolith for liquid chromatography as in claim 1 wherein Z is a cation or an anion.

7. A monolith for liquid chromatography as in claim 1 wherein Z is sulfonate (—SO$_2$OH), carboxylate (—COOH), or phosphate (—PO(OH)$_2$).

8. A monolith for liquid chromatography as in claim 1 wherein the crosslinker comprises one or more selected from the group consisting of;

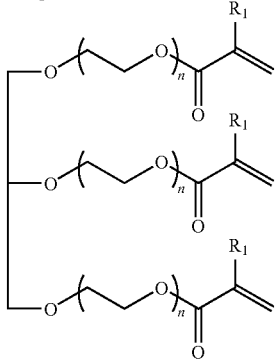

where in each chain n is the same or different and is at least 1, $R_1$ in each pendant group is the same or different and is H, or $CH_3$, and

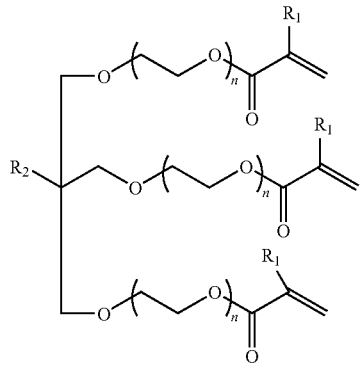

where in each chain n is the same or different and is at least 1, $R_1$ in each pendant group is the same or different and is H, or $CH_3$, and $R_2$ is $CH_2OH$ or another hydrophilic group, and

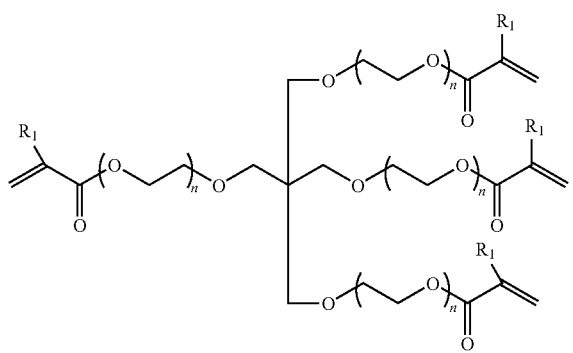

where n is at least 1 and the same or different in each chain, and $R_1$ in each chain is the same or different and is H, or $CH_3$.

9. A monolith for liquid chromatography as in claim 1 wherein the crosslinker comprises one or more selected from the group consisting of;

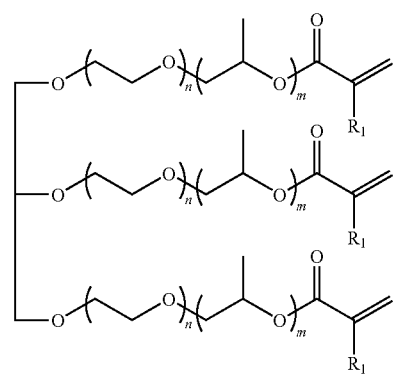

and

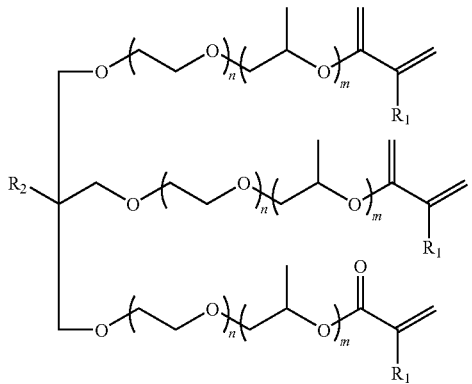

and

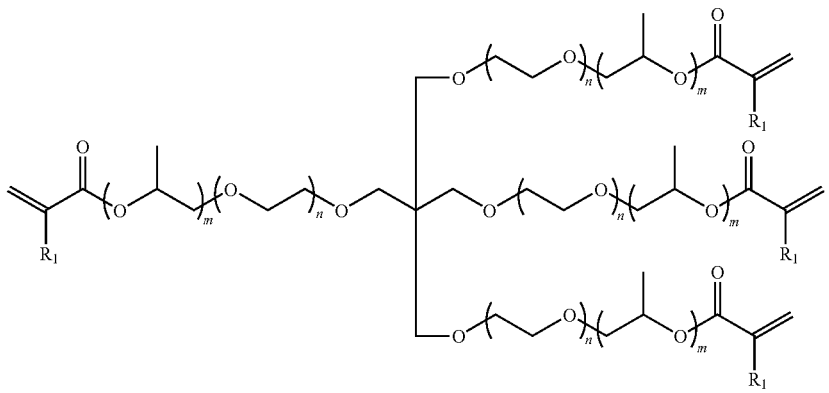

where n and m represent are the same or different and are 0 or greater, and n+m is equal to or greater than 3, $R_1$ is s H or $CH_3$.

10. A monolith for liquid chromatography as in claim 1 wherein Z is $-NH_2$, $-NHR_1$, $-NR_1R_2$, or $-NR_1R_2R_3^+$, where $R_1$, $R_2$, and $R_3$ are the same or different and are methyl or ethyl.

11. A monolith for liquid chromatography as in claim 1 wherein Z is a chiral selector.

12. A monolith for liquid chromatography as in claim 1 wherein Z is a hydrophobic alkyl chains of the formula, $-(CH_2)_n-CH_3$, where n=3-17.

13. A monolith for liquid chromatography as in claim 1 wherein Z is a hydrophobic alkyl chain of the formula $-(CH_2)_n-CH_3$, where n=1-7, or is phenyl.

14. A monolith for liquid chromatography as in claim 1 wherein Z is $CH_3$ or —H.

15. A monolith for liquid chromatography as in claim 1 wherein the monomer is poly(ethylene glycol) methyl ether acrylate.

16. A monolith for liquid chromatography as in claim 1 wherein the monomer is

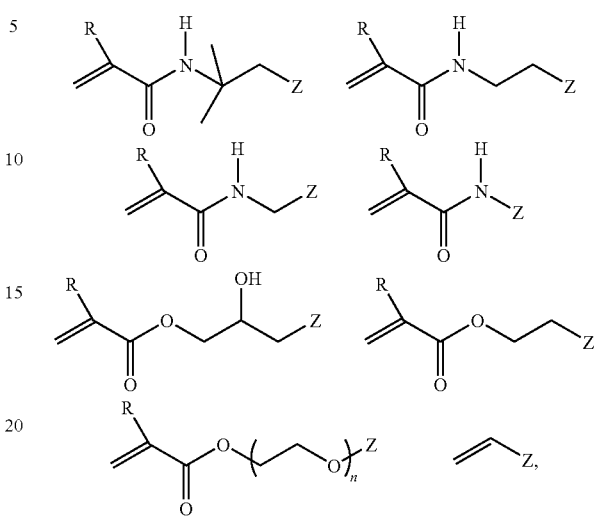

where R is $CH_3$ or H.

* * * * *